(12) United States Patent
Womack et al.

(10) Patent No.: US 8,557,262 B2
(45) Date of Patent: Oct. 15, 2013

(54) DIVINYL ETHER DERIVATIVES CAPABLE OF RELEASING ACTIVE ALDEHYDES AND KETONES AND METHODS OF USE FOR PERFUMING SURFACES

(75) Inventors: Gary Bernard Womack, Hopewell, NJ (US); Robert Langley Fuller, Asbury, NJ (US); Glenn Paul Johannes Verhovnik, Chene-Bougeries (CH); Nathalie Pinel, Neydens (FR); Magali Lateulere, Nyon (CH); Marie Buy, Annemasse (FR)

(73) Assignee: Firmenich SA, Geneva (CH)

( * ) Notice: Subject to any disclaimer, the term of this patent is extended or adjusted under 35 U.S.C. 154(b) by 232 days.

(21) Appl. No.: 13/057,416

(22) PCT Filed: Aug. 31, 2009

(86) PCT No.: PCT/IB2009/053790
§ 371 (c)(1), (2), (4) Date: Feb. 3, 2011

(87) PCT Pub. No.: WO2010/029462
PCT Pub. Date: Mar. 18, 2010

(65) Prior Publication Data
US 2011/0142776 A1  Jun. 16, 2011

Related U.S. Application Data

(60) Provisional application No. 61/096,544, filed on Sep. 12, 2008.

(30) Foreign Application Priority Data
Sep. 12, 2008  (WO) ............... PCT/IB2008/053695

(51) Int. Cl.
| | | |
|---|---|---|
| A61K 8/02 | (2006.01) |
| A61K 9/14 | (2006.01) |
| A61K 8/19 | (2006.01) |
| A61K 31/74 | (2006.01) |
| A61Q 1/12 | (2006.01) |
| A61Q 5/00 | (2006.01) |
| A61Q 9/00 | (2006.01) |
| C08G 8/02 | (2006.01) |
| C08G 14/02 | (2006.01) |
| C07C 47/00 | (2006.01) |
| C07C 49/00 | (2006.01) |
| C07C 205/00 | (2006.01) |

(52) U.S. Cl.
USPC ............ 424/401; 424/484; 424/69; 424/70.1; 424/73; 424/78.31; 106/31.02; 528/125; 528/129; 568/579; 568/303; 568/306; 568/307; 568/325; 568/420; 568/425; 568/442

(58) Field of Classification Search
USPC ................ 424/401, 484, 69, 70.1, 73, 78.31; 106/31.02; 528/125, 129; 568/579, 568/303, 306, 307, 325, 420, 425, 442
See application file for complete search history.

(56) References Cited

U.S. PATENT DOCUMENTS

| 3,256,344 A | 6/1966 | McTeer .......................... 260/614 |
| 4,891,451 A | 1/1990 | Hoelderich et al. .......... 568/691 |

(Continued)

FOREIGN PATENT DOCUMENTS

| DE | 30 03 494 A1 | 8/1980 |
| EP | 0 936 211 B1 | 8/1999 |

(Continued)

OTHER PUBLICATIONS

Adam et al., "Photochemistry of Bis(2-methyl-1-propenyl)ether and 2,2,4,4-tetramethyl-6-oxabicyclo[3.1.0]hexan-3-one: on the search for the oxydi-pi-methane rearrangement," 1985; Tetrahedron Letters, 26(5): 619-622.*

(Continued)

Primary Examiner — Jane C Oswecki
(74) Attorney, Agent, or Firm — Winston & Strawn LLP

(57) ABSTRACT

The present invention provides divinyl ether derivatives capable of releasing in a controlled manner at least one active aldehyde and/or ketone into the surrounding environment. The invention relates to the use of these divinyl ether derivatives as perfuming or flavoring ingredients, as well as to the perfuming compositions and consumer articles containing them.

16 Claims, 11 Drawing Sheets

(56) References Cited

U.S. PATENT DOCUMENTS

| | | | | |
|---|---|---|---|---|
| 5,649,979 | A | 7/1997 | Paget et al. | 8/137 |
| 5,767,325 | A | 6/1998 | Schröder et al. | 568/691 |
| 6,133,228 | A | 10/2000 | Pika et al. | 512/21 |
| 6,218,355 | B1 | 4/2001 | Herrmann | 512/27 |
| 6,369,026 | B1 | 4/2002 | Pika et al. | 512/21 |
| 7,175,871 | B2 * | 2/2007 | Mookherjee et al. | 426/534 |
| 7,723,286 | B2 | 5/2010 | Fehr et al. | 512/8 |
| 2004/0102357 | A1 | 5/2004 | Smith et al. | 512/3 |
| 2010/0098650 | A1 | 4/2010 | Herrmann et al. | 424/65 |

FOREIGN PATENT DOCUMENTS

| | | |
|---|---|---|
| EP | 0 971 021 A1 | 1/2000 |
| GB | 2 041 964 A | 9/1980 |
| WO | WO 95/04809 A1 | 2/1995 |
| WO | WO 95/08976 A1 | 4/1995 |
| WO | WO 98/47477 A1 | 10/1998 |
| WO | WO 99/60990 A2 | 12/1999 |
| WO | WO 01/28980 A1 | 4/2001 |
| WO | WO 03/049666 A2 | 6/2003 |
| WO | WO 2008/093272 A2 | 8/2008 |

OTHER PUBLICATIONS

Garza-Ulloa et al., "Oxidation of Beer", Apr. 1976; The Brewers Digest, pp. 48-49 and 72.*

Garza-Ulloa et al., "Oxidation of Beer," Apr. 1976; The Brewers Digest, pp. 48-49 and 72.*

Adam et al., "Photochemistry of Bis(2-methyl-1-propenyl)ether and 2,2,4,4-tetramethyl-6-oxobicyclo[3.1.0]hexan-3-one: on the search for the oxydi-pi-methane rearrangement," 1985; Tetrahedron Letters, 26(5): 619-622.*

Kulkarni et al., Tetrahedron Letters, 2003; 44(26): 4913-4914.*

International Search Report and Written Opinion of the International Searching Authority, application No. PCT/IB2009/053790, mailed Jan. 29, 2010.

Adam et al., "Photochemistry of bis(2-methyl-1-propenyl)ether and 2,2,4,4-tetramethyl-6-oxabicyclo [3.1.0] hexan-3-one: on the search for the oxydi-π-methane rearrangement," Tetrahedron Letters, 26(5):619-622 (1985).

Aitken et al., "Flash vacuum pyrolysis over magnesium. Part 1. Pyrolysis of benzylic, other aryl/alkyl and aliphatic halides," J. Chem. Soc., Perkin Trans. 1, 402-415 (2002).

Garza-Ulloa et al., "Oxidation of beer; 2-trans-nonenal and 2-trans-6-cis-nonadienal as decomposition products from a mixture of colneleic and colnelenic acids," Brewers' Digest, 51(4):48-49, 72 (1976).

* cited by examiner

DIVINYL ETHER DERIVATIVES CAPABLE OF RELEASING ACTIVE ALDEHYDES AND KETONES AND METHODS OF USE FOR PERFUMING SURFACES

This application is a 371 filing of International Patent Application PCT/IB2009/053790 filed Aug. 31, 2009, which claims the benefit of application No. 61/096,544 filed Sep. 12, 2008.

TECHNICAL FIELD

The present invention provides divinyl ether derivatives capable of releasing in a controlled manner at least one active aldehyde and/or ketone into the surrounding environment. The invention relates to the use of these divinyl ether derivatives as perfuming or flavoring ingredients, as well as to the perfuming compositions and consumer articles containing them.

PRIOR ART

To the best of our knowledge, none of the compounds of formula (I), as described below are known in the prior art as being useful in the field of perfumery and in particular as being capable of liberating active aldehydes and/or ketones under certain application conditions.

Many perfumery active compounds are highly volatile and can thus only be perceived over a limited period of time. Extensive research has therefore been performed in order to find new efficient precursors allowing a controlled release of active volatile molecules, particularly in the field of perfumery and flavoring. The prior art discloses many such precursors, which are able to prolong or enhance the effect of active molecules such as fragrances. Nevertheless none of the prior art documents discloses the divinyl ethers used in the present invention as precursors for the controlled release of aldehydes and/or ketones, so as to prolong the perfuming effect of the latter upon application thereof onto varied surfaces.

U.S. Pat. No. 7,175,871 discloses several enol ethers, their use as perfuming ingredients, as well as perfuming compositions and perfuming or perfumed articles comprising them. Such compositions and articles, as well as their use for perfuming surfaces, are therefore hereby disclaimed. Nevertheless, this document deals only with the use of such compounds in perfumes and is totally silent with regard to the ability of any of the disclosed compounds, or their analogues, to release active aldehydes and/or ketones in a controlled manner In fact, this prior art document clearly implies that the disclosed compounds cannot be used to release volatile compounds, by clearly stating on column 2 lines 21 to 24, that the compounds have "sustainable heat, light and base stability", meaning that they are not susceptible of chemical degradation such as is needed to release an active aldehyde and/or ketone.

Other prior art discloses quite a few compounds structurally related to the compounds used in the present invention. Nevertheless, these prior art disclosures are totally unrelated to the object of the present invention, i.e. the use of the compounds of formula (I), as described below, as precursors of odorant aldehydes and/or ketones. For example R. A. Aitken, P. K. G. Hodgson, J. J. Morrison and A. O. Oyewale, Flash vacuum pyrolysis over magnesium; Part 1: Pyrolysis of benzylic, other aryl/alkyl and aliphatic halides, J. Chem. Soc., Perkin Trans. 1, 2002, 402-415 discloses a process for preparing different compounds among which dihex-1-enyl ether (see scheme 18, compound n° 63). U.S. Pat. No. 3,256,344 discloses a process for preparing di(1,2-olefinically unsaturated aliphatic) ethers and in particular di(alkadienyl) ethers. U.S. Pat. No. 5,767,325 and U.S. Pat. No. 4,891,451 describe processes for the preparation of enol ethers and the corresponding products. None of these documents discloses or suggests the use in perfumery of the compounds used in the invention, nor their capability to release at least one active aldehyde and/or ketone and more particularly a perfuming one.

DESCRIPTION OF THE INVENTION

Surprisingly, we have now found that the divinyl ether derivatives described below are capable of an efficient release of at least one active aldehyde and/or ketone in application. The compounds used in the present invention thus increase the long-lastingness of such aldehydes and/or ketones in applications by providing a controlled release system of these active volatile compounds. Moreover, the divinyl ethers used in the present invention also make it possible to render more stable in application the corresponding aldehyde and/or ketones to be released.

By the term "active" we mean here that the aldehyde or ketone to which it refers is capable of bringing a benefit or effect into its surrounding environment, and in particular a perfuming, flavoring, masking, insect repellent or attractant, bactericide, insecticide, fungicide and/or malodor counteracting effect. Therefore, for example, said "active aldehyde and/or ketone" possesses at least one property which renders it useful as perfuming or flavoring ingredient, as insect repellent or attractant, as insecticide, bactericide or fungicide, or as malodor counteractant. Preferred active aldehydes and ketones are perfuming or flavoring ingredients, insect repellents or attractants, or malodor counteractants. Particularly preferred active aldehydes and ketones are perfuming or flavoring ingredients, or yet malodor counteractants.

By the term "malodor counteractant" or "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor.

According to all the above and below mentioned embodiments of the invention, the compounds (I), as defined below, are particularly useful when the active aldehyde or ketone is a perfuming ingredient, i.e. a perfuming aldehyde. A "perfuming aldehyde" is a compound which is of current use in the perfumery industry, i.e. a compound which is used as active ingredient in perfuming preparations or compositions in order to impart a hedonic effect when applied on a surface. In other words, such an aldehyde or ketone, to be considered as being a perfuming one, must be recognized by a person skilled in the art of perfumery as being able to impart or modify in a positive or pleasant way the odor of a composition or of an article or surface, and not just as having an odor. Moreover, this definition is also meant to include compounds that do not necessarily have an odor but are capable of modulating the odor of a perfuming composition, perfumed article or surface and, as a result, of modifying the perception by a user of the odor of such a composition, article or surface.

The invention is carried out exactly in the same manner, independently of the exact properties of the active aldehyde or ketone. Therefore, it is hereby understood that, even if the invention is further illustrated herein below with a specific reference to "perfuming aldehydes and/or ketones", the below embodiments are also applicable to other active aldehydes and/or ketones (i.e. it is possible to replace the expression "perfuming" with "flavoring", "insect attractant", "insect repellent", "masking", "fungicide", "insecticide" "bactericide" or with "malodor counteractant", for instance).

The invention relates to the use of a compound defined by the following formula

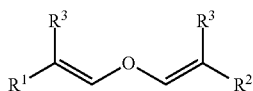

(I)

wherein $R^1$ and $R^2$ are identical or different and represent each a $C_2$ to $C_{15}$ hydrocarbon group optionally comprising an oxygen atom and each of the groups $R^3$ represents a hydrogen atom or a methyl group, for the controlled release of at least one active aldehyde and/or ketone selected form
an active aldehyde of formula

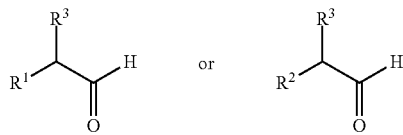

(II)

wherein $R^1$, $R^2$ and $R^3$ have the same meaning as in formula (I); and/or
an active aldehyde or ketone of formula

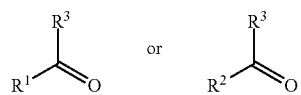

(III)

wherein $R^1$, $R^2$ and $R^3$ have the same meaning as in formula (I).

The groups $R^1$ and $R^2$ can be very general since they are essentially derived from any aldehyde or ketone possibly useful in perfumery.

According to a preferred embodiment of the invention, the compounds of formula (I) are those wherein $R^1$ and $R^2$ are identical and represent a $C_6$ to $C_{15}$ hydrocarbon group, optionally comprising an oxygen atom.

According to a more preferred embodiment, $R^1$ and $R^2$ are identical and are selected from the group consisting of a) a $C_6$ to $C_{15}$, preferably a $C_6$ to $C_{10}$ linear, branched or cyclic alkyl or alkenyl group, optionally comprising an oxygen atom, even more preferably a $C_6$ to $C_{10}$ linear or branched alkyl or alkenyl group, optionally comprising an oxygen atom;

b) a $C_2$ to $C_9$ linear, branched or cyclic alkyl or alkenyl group substituted with one or more phenyl groups and optionally comprising an oxygen atom, preferably a $C_2$ to $C_6$ linear, branched or cyclic alkyl or alkenyl group substituted with one phenyl group and optionally comprising an oxygen atom, more preferably a $C_2$ to $C_4$ linear, branched or cyclic alkyl or alkenyl group substituted with one phenyl group and optionally comprising an oxygen atom, even more preferably a $C_2$ to $C_4$ linear or branched alkyl or alkenyl group, substituted with one phenyl group and most preferably a $C_2$ to $C_4$ linear or branched alkyl group substituted with one phenyl group;

c) a benzyl group, optionally substituted with up to 8 carbon atoms and optionally substituted with an oxygen containing group, preferably an unsubstituted benzyl group; and d) a phenyl group, optionally substituted with up to 9 carbon atoms and optionally substituted with an oxygen containing group, preferably an unsubstituted phenyl group.

According to a preferred embodiment, the $R^1$ and $R^2$ groups, as defined above, do not contain any oxygen atom.

According to a more preferred embodiment, the $R^1$ and $R^2$ groups are selected from the group consisting of the hexyl group, the heptyl group, the octyl group, the nonyl group, the decyl group, the benzyl group, the 1-phenylethyl group, the 1-methyl-3-phenylpropyl group, the 4-heptenyl group, the 1,3,3-trimethylbutyl group, the 7-nonenyl group, the 8-nonenyl group, the 4-tert-butylbenzyl group, the 2-phenylethyl group, the phenyl group, the 4-hexenyl group, the 3-hexenyl group, the 2,2-dimethylpropyl group, the 6-octenyl group, the 7-octenyl group and the 4-tert-butylphenyl group.

According to another preferred embodiment, the $R^3$ group represents a hydrogen atom.

As examples of compounds of formula (I), one may cite 1,1'-oxybis-1-decene, 1,1'-oxybis-1-octene, 1,1'-oxybis-1-nonene, 1,1'-oxybis-1-undecene, 1,1'-oxybis-1-decene, 1,1'-oxybis(2-methyl-1-decene), 1,1'-oxybis(2-methyl-1-undecene), 1,1'-[oxybis(1-propene-1,3-diyl)]dibenzene, 1,1'-[oxybis(1-butene-1,3-diyl)]dibenzene, 1,1'-[oxybis(2-methyl-1-butene-1,4-diyl)]dibenzene, 1,1'-[oxybis(3-methyl-1-pentene-1,5-diyl)]dibenzene, 1,1'-oxybis(1,6-nonadiene), 1,1'-oxybis(3,5,5-trimethyl-1-hexene), 1,1'-oxybis(1,9-undecene), 1,1'-oxybis(1,10-undecene) and 1,1'-[oxybis(1-propene-1,3-diyl)]bis(4-tert-butylbenzene).

More specifically, 1,1'-oxybis-1-decene, 1,1'-oxybis-1-nonene, 1,1'-oxybis-1-undecene, 1,1'-oxybis(2-methyl-1-undecene) 1,1'-[oxybis(1-propene-1,3-diyl)]dibenzene, 1,1'-[oxybis(1-butene-1,3-diyl)]dibenzene, 1,1'-[oxybis(3-methyl-1-pentene-1,5-diyl)]dibenzene, 1,1'-oxybis(1,9-undecene), 1,1'-oxybis(1,10-undecene) and 1,1'-[oxybis(1-propene-1,3-diyl)]bis(4-tert-butylbenzene) can be advantageously used according to the invention.

1,1'-[Oxybis(1-propene-1,3-diyl)]dibenzene, 1,1'-[oxybis(1-butene-1,3-diyl)]dibenzene, 1,1'-[oxybis(3-methyl-1-pentene-1,5-diyl)]dibenzene and 1,1'-oxybis(1,9-undecene) are even more advantageously used according to the invention.

According to any of the embodiments, the compounds of formula (I) are advantageously characterized by a vapor pressure below 0.01 Pa, as obtained by calculation using the software EPIwin v. 3.10 (2000, available at the US Environmental Protection Agency). According to a preferred embodiment, said vapor pressure is below 0.001 Pa.

As mentioned above the compound (I) is capable of releasing at least one active aldehyde or ketone. According to a particular embodiment of the invention, said active aldehyde or ketone is advantageously characterized by a vapor pressure above 2.0 Pa, as obtained by calculation using the software EPIwin v. 3.10 (2000, available at the US Environmental Protection Agency). According to another embodiment, said vapor pressure is above 5.0, or even above 7.0 Pa.

In an even more preferred embodiment, said active aldehydes of formula (II) or (III) are selected from the group of aldehydes of formula RCHO, wherein R is a linear or α-branched alkyl group of $C_6$ to $C_{12}$, 3-(1,3-benzodioxol-5-yl)-2-methylpropanal, 4-decenal, 8-decenal, 9-decenal, 3-(6,6-dimethyl-bicyclo[3.1.1]hept-2-en-2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 5,9-dimethyl-4,8-decadienal, 2,6-dimethyl-5-heptenal (melonal), 3,7-dimethyloctanal, 3,7-dimethyl-6-octenal (citronellal), (3,7-dimethyl-6-octenyl)acetaldehyde, 3-dodecenal, 4-dodecenal, 4-heptenal, 7-hydroxy-3,7-dimethyloctanal (hydroxycitronellal), 4- and 3-(4-hydroxy-4-methylpentyl)-3-cyclohexene-1-carbaldehyde (Lyral®, origin: International Flavors and Fragrances, New York, USA), 3-(4-isopropylphenyl)-2-methylpropanal, 2-(4-isopropylphenyl) propanal, (4R)-1-p-menthene-9-carbaldehyde (Liminal®, origin: Firmenich SA, Geneva, Switzerland), 6-methoxy-2,6-dimethylheptanal (methoxymelonal), 8 (9)-methoxy-tricyclo[5.2.1.0.(2,6)]decane-3(4)-carbaldehyde (Scentenal®, origin: Firmenich SA, Geneva, Switzerland), 2-(4-methylenecyclohexyl)propanal, 4-(4-methyl-3-pentenyl)-3-cyclohexene-1-carbaldehyde (Acropal®, origin: Givaudan-Roure SA., Vernier, Switzerland), (4-methylphenoxy)acetaldehyde, (4-methylphenyl)acetaldehyde, 3-methyl-5-phenylpentanal, 6-nonenal, 8-nonenal, phenoxyacetaldehyde, phenylacetaldehyde, 3-phenylbutanal (Trifernal®, origin: Firmenich SA, Geneva, Switzerland), 3-phenylpropanal, 2-phenylpropanal (hydratropaldehyde), 3-(4-tert-butylphenyl)-2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0 (2,6)]decane-4-carbaldehyde, exo-tricyclo[5.2.1.0(2,6)]decane-8-exo-carbaldehyde (Vertral®, origin: Symrise, Holzminden, Germany), 2,6,6-trimethyl-bicyclo[3.1.1]heptane-3-carbaldehyde (formyl pinane), 2,4,6- and 3,5,6-trimethyl-3-cyclohexene-1-carbaldehyde, 2,2,3-trimethyl-3-cyclopentene-1-acetaldehyde (campholenic aldehyde), 2,5,6-trimethyl-4-heptenal, 3,5,5-trimethylhexanal, 2,6,10-trimethyl-9-undecenal, 10-undecenal or 9-undecenal and their mixtures such as Intreleven aldehyde (origin: International Flavors & Fragrances, New York, USA); wherein the underlined compounds represent, in an even more preferred embodiment of the invention, particularly useful fragrance aldehydes.

Owing to their particular chemical structure, the compounds (I) are capable of releasing a residue and at least one active aldehyde and/or ketone. This may happen via an oxydative decomposition reaction, which is believed to be influenced by light exposure, but may also be triggered by heat, pH change and/or other types of mechanisms.

A compound of formula (I) may release a mixture of aldehydes and/or ketones with a diverse number of carbon atoms. In particular, a compound of formula (I) may release an aldehyde having the same number of carbon atoms as the aldehyde from which the divinyl ether is prepared and/or aldehydes or ketones having one or even two carbon atoms less. This means that a compound of formula (I) may release aldehydes of formula (II) and/or aldehydes or ketones of formula (III), optionally with $R^1$ or $R^2$ groups of different lengths.

As mentioned above, the invention concerns the use of the above-described compounds of formula (I) for the controlled release of a perfuming ingredient. In other words it concerns a method to confer, enhance, improve or modify the odor properties of a perfuming composition, of an article or of a surface, by the controlled release of a perfuming aldehyde, which method comprises adding to said composition or article an effective amount of at least a compound (I), provided that compounds of formula (I), wherein $R^1$ is a $C_8$ mono alkenyl group and $R^2$ is selected from the group consisting of the $C_4$ to $C_{10}$ alkyl groups and the $C_9$ 8-alken-1-yl group, are excluded, or treating a surface with said composition or article.

By "use of a compound (I)" it is understood here also the use of any composition containing said compounds and which can be advantageously employed in the perfume industry in particular.

Said compositions, which in fact can be advantageously employed as perfuming ingredients, are also an object of the present invention.

Therefore, another object of the present invention is a perfuming composition comprising:
a) at least one compound of formula (I) as defined above, provided that compounds of formula (I), wherein $R^1$ is a $C_8$ mono alkenyl group and $R^2$ is selected from the group consisting of the $C_4$ to $C_{10}$ alkyl groups and the $C_9$ 8-alken-1-yl group, are excluded;
b) at least one ingredient selected from the group consisting of a perfumery carrier and a perfumery base; and
c) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

Generally speaking, by "perfumery base" we mean here a composition comprising at least one perfuming co-ingredient together with compound or compounds (I).

Said perfuming co-ingredient is not a compound (I). Moreover, by "perfuming co-ingredient" it is meant here a compound which is used in a perfuming preparation or composition to impart a hedonic effect. In other words such a co-ingredient, in order to be considered as a perfuming ingredient, must be recognized by a person skilled in the art as being able to impart or modify in a positive, desirable or pleasant way the odor of a composition, article or surface on which it is applied, and not just as having an odor.

The nature and type of the perfuming co-ingredients present in the base does not warrant a more detailed description here, which in any case would not be exhaustive, the skilled person being able to select them on the basis of its general knowledge, the intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

Generally speaking, by "perfumery adjuvant" we mean here an ingredient capable of imparting an-added benefit such as a color, a particular light resistance, chemical stability, etc.

A detailed description of the nature and type of adjuvant commonly used in perfuming bases cannot be exhaustive, but such ingredients are well known to a person skilled in the art.

A composition consisting of at least one of the compounds (I), provided that compounds of formula (I), wherein $R^1$ is a $C_8$ mono alkenyl group and $R^2$ is selected from the group consisting of the $C_4$ to $C_{10}$ alkyl groups and the $C_9$ 8-alken-1-yl group, are excluded, and at least one perfumery carrier, represents a particular embodiment of the invention. Another embodiment of the invention is one such perfuming composition further comprising at least one perfumery base, and optionally at least one perfumery adjuvant.

It is useful to mention here that the possibility of the compositions mentioned above comprising mixtures of two or more compounds (I) is important, as it enables the perfumer to prepare accords and perfumes possessing the odor tonality of various compounds (I), thus creating new tools for their perfuming palette. In addition, compounds (I) may also be used in admixture with other chemical or physical release systems for perfuming ingredients. They may for example be combined with encapsulated ingredients, preferably of a different nature, or yet with the many known release systems wherein the active ingredient is released as a result of a chemical or photochemical reaction. Examples of such release systems are found for example in WO 95/04809, EP 0971021, WO 03/049666, EP 0936211, WO 99/60990, WO 01/28980, WO 08/093272, WO 98/47477, US 2004/0102357, DE 30 03 494 and WO 95/08976, provided that such mixtures are incorporated in end consumer products that, under the conditions of their application onto surfaces, allow the release of the corresponding active perfuming ingredient.

Furthermore, a compound (I) or a perfuming composition comprising a compound (I), provided that compounds of formula (I) wherein $R^1$ is a $C_8$ mono alkenyl group and $R^2$ is selected from the group consisting of the $C_4$ to $C_{10}$ alkyl groups and the $C_9$ 8-alken-1-yl group, are excluded, is a useful perfuming ingredient, which can be advantageously used in all the fields of modern perfumery, such as fine perfumery or functional perfumery. Indeed, the compounds (I) and the perfumes containing them may be advantageously employed in fine or functional perfumery to achieve a more controlled deposition, and consequent release, of perfuming aldehydes or ketones.

For example, the compounds (I), owing to a good substantivity, low volatility and a capability to provide release of odoriferous or odor impacting molecules, can be incorporated in any application requiring the effect of rapid or prolonged liberation of an odoriferous component as defined hereinabove and furthermore can impart a fragrance and a freshness to a treated surface which will last well beyond the treatment period, for example in laundry or body care processes, well beyond the surface rinsing and/or drying processes. Suitable application surfaces for the perfuming ingredients of the invention are, in particular, textiles, hard surfaces such as glass windows, kitchen and bathroom surfaces, hair and skin.

Consequently, an article comprising:
a) at least one compound of formula (I), as defined above, or a perfuming composition of the invention, as defined above; and
b) a consumer product base;
is also an object of the present invention, as is the use of such a composition for the treatment of a surface such as those above-mentioned.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a hair or body care product such as a shampoo or shower gel, a detergent or an air freshener, together with an olfactively effective amount of at least one compound (I).

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners, heavy duty cleaners, as well as all the other articles common in perfumery, namely perfumes, colognes or after-shave lotions, perfumed soaps, shower or bath salts, mousses, creams, oils or gels, hygiene products or hair care products such as shampoos, body-care products, deodorants or antiperspirants, air fresheners and also cosmetic preparations. As detergents it is intended to include here applications such as detergent compositions or cleaning products for washing up, cleaning or treating various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the compounds (I), so that it may be necessary to protect the latter from premature decomposition, for example by encapsulation.

Preferred perfumed articles are perfumes, colognes, after-shave lotions, perfumed soaps, shower or bath salts, mousses, creams, oil or gels, hygiene products, or hair care products such as shampoos and other hair treatment products, or yet body-care products such as deodorants or antiperspirants.

The proportions in which the compounds (I) can be incorporated into the various aforementioned articles or compositions vary within a wide range of values. These values are dependent upon the nature of the article or product into which they are to be incorporated and on the desired olfactory effect, as well as the nature of the co-ingredients in a given composition, when the compounds (I) are mixed with perfuming co-ingredients, solvents or additives commonly used in the art.

For example, typical concentrations of compound (I) in a perfuming composition of the invention may vary in a wide range of values, comprised between 1% and 40% by weight, preferably of 5% to 20% by weight, relative to the weight of the perfuming composition. Concentrations lower than these, such as in the order of 0.001% to 5%, more preferably of 0.3 to 2%, or even 0.5 to 1%, by weight, relative to the total weight of consumer product, can be used when these compounds are applied directly in the perfuming of the various consumer products mentioned hereinabove.

Another object of the present invention relates to a method for the perfuming of a surface or to a method for intensifying or prolonging the diffusion effect of the characteristic fragrance of at least one odoriferous aldehyde or ketone selected from aldehydes of formula (II) and aldehydes or ketones of formula (III), on a surface, characterized in that said surface is treated with a compound (I) or with a composition or article as defined above which contain the compound (I), under conditions which are susceptible of allowing the release of said aldehyde and/or ketone, as defined above. Suitable surfaces for such treatment are, in particular, textiles, hard surfaces, hair and skin. According to a particular embodiment of such a treatment method, the conditions under which the compounds (I), or the compositions or articles containing them, are applied to a particular surface, require the use of light.

According to another embodiment, the invention relates to a compound selected from the group consisting of 1,1'-oxybis-1-decene, 1,1'-oxybis-1-octene, 1,1'-oxybis-1-nonene, 1,1'-oxybis-1-undecene, 1,1'-oxybis(2-methyl-1-decene), 1,1'-oxybis(2-methyl-1-undecene), 1,1'-[oxybis(1-propene-1,3-diyl)]dibenzene, 1,1'-[oxybis(1-butene-1,3-diyl)]dibenzene, 1,1'-[oxybis(2-methyl-1-butene-1,4-diyl)]dibenzene, 1,1'-[oxybis(3-methyl-1-pentene-1,5-diyl)]dibenzene, 1,1'-oxybis(1,6-nonadiene), 1,1'-oxybis(3,5,5-trimethyl-1-hexene), 1,1'-oxybis(1,9-undecene), 1,1'-oxybis(1,10-undecene) and 1,1'-[oxybis(1-propene-1,3-diyl)]bis(4-tert-butylbenzene).

Preferably, the compound is selected from the group consisting of 1,1'-oxybis-1-decene, 1,1'-oxybis-1-nonene, 1,1'-oxybis-1-undecene, 1,1'-oxybis(2-methyl-1-undecene) 1,1'-[oxybis(1-propene-1,3-diyl)]dibenzene, 1,1'-[oxybis(1-butene-1,3-diyl)]dibenzene, 1,1'-[oxybis(3-methyl-1-pentene-1,5-diyl)]dibenzene, 1,1'-oxybis(1,9-undecene), 1,1'-oxybis(1,10-undecene) and 1,1'-[oxybis(1-propene-1,3-diyl)]bis(4-tert-butylbenzene). It is even more preferably selected from the group consisting of 1,1'-[oxybis(1-propene-1,3-diyl)]dibenzene, 1,1'-[oxybis(1-butene-1,3-diyl)]dibenzene, 1,1'-[oxybis(3-methyl-1-pentene-1,5-diyl)]dibenzene and 1,1'-oxybis(1,9-undecene).

The compounds (I) can be prepared according to the general method described in U.S. Pat. No. 3,256,344.

BRIEF DESCRIPTION OF THE DRAWING FIGURES

FIG. 1 discloses GC-MS data that shows that at elevated light exposure (LUX) 1,1'-oxybis-1-decene decomposed more completely into the aldehyde decanal and nonanal;

FIG. 2 discloses GC-MS data that the light effect on fragrance release for phenylpropanal divinyl ether;

FIGS. 3 and 4 provide data that indicates the release of aldehydes from a divinyl ether when the latter was combined with a fragrance;

FIG. 5 provides data that shows the release of free aldehydes from 1,1'-oxybis-1-undecene;

PREPARATION OF COMPOUNDS

Figure 1:
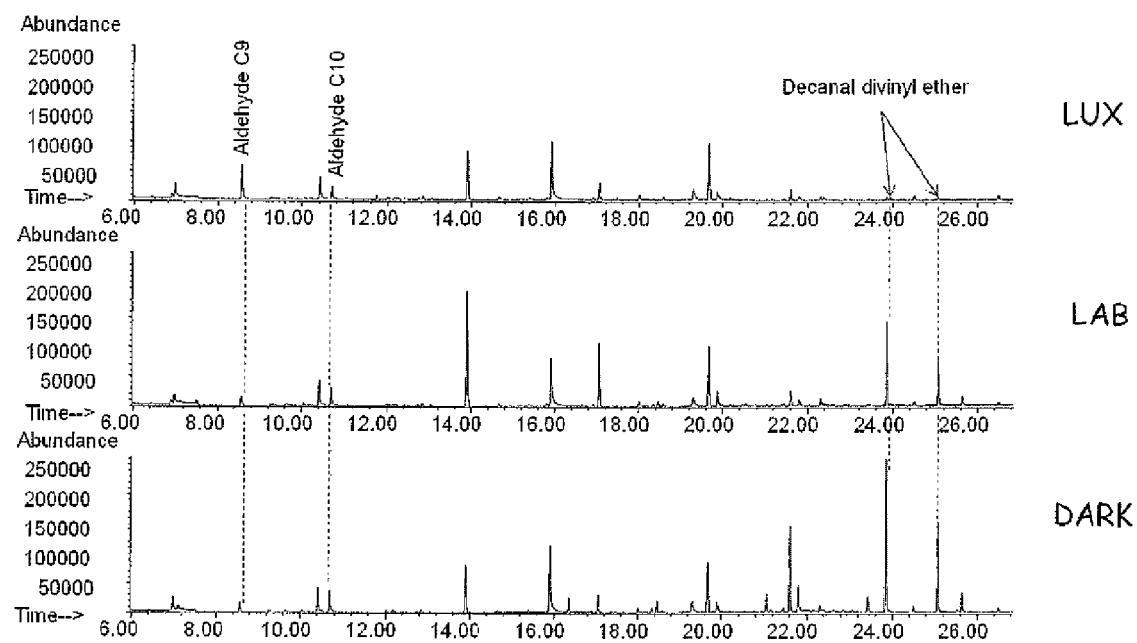

The following compounds have been thus prepared, and characterized. Mass spectral data (EI, 70 eV) is provided for the major isomer only (generally the Z,E-isomer). NMR spectra were recorded at 400 MHz for $^1$H and 100 MHz for $^{13}$C using CDCl$_3$ as solvent. The chemical displacements δ are indicated in ppm with respect to TMS as standard, the coupling constants J are expressed in Hz.

1. 1,1'-oxybis-1-decene, Prepared From Decanal
MS: 294 (M$^+$, 10), 195 (8), 138 (16), 97 (43), 83 (100), 69 (49), 57 (47), 55 (56), 41 (38). $^1$H NMR: 0.88 (t, J=6.7, 6H); 1.20-1.45 (m, 24H); 1.88-1.96 (m) and 2.06-2.16 (m) (4H); 4.46 (q, J=6.1), 4.52 (q, J=6.1), 5.04 (dt, J=12.3, J=7.7) and 5.06 (dt, J=12.3, J=7.7) (=CHR, 2H); 6.09 (d, J=6.1), 6.12 (d, J=6.1), 6.21 (d, J=12.3), 6.26 (d, J=12.3) (OCH=, 2H).
$^{13}$C NMR: 14.1 (q), 22.72 (t), 23.97 (t), 24.02 (t), 27.39 (t), 29.09 (t), 29.28 (t), 29.39 (t), 29.48 (t), 29.59 (t), 29.64 (t), 30.25 (t), 30.33 (t), 31.94 (t), 31.98 (t), 108.5 (d), 108.8 (d), 109.7 (d), 110.1 (d), 141.5 (d), 142.9 (d), 143.2 (d), 144.3 (d).

2. 1,1'-oxybis-1-octene, Prepared from Octanal
MS: 238 (M$^+$, 14), 167 (10), 111 (28), 110 (25), 81 (27), 69 (100), 57 (31), 55 (48), 41 (34).
$^1$H NMR: 0.88 (t) and 0.89 (t, J=6.7) (6H); 1.20-1.45 (m, 16H); 1.88-1.97 (m) and 2.06-2.17 (m) (4H); 4.47 (q, J=6.1), 4.52 (q, J=6.1), 5.04 (dt, J=12.3, J=7.6) and 5.06 (dt, J=12.3, J=7.6) (=CHR, 2H); 6.08 (d, J=6.1), 6.12 (d, J=6.1), 6.21 (d, J=12.3), 6.26 (d, J=12.3) (OCH=, 2H).
$^{13}$C NMR: 14.1 (q), 22.68 (t), 23.98 (t), 24.03 (t), 27.38 (t), 28.76 (t), 28.93 (t), 29.55 (t), 29.61 (t), 30.22 (t), 30.28 (t), 31.74 (t), 108.5 (d), 108.8 (d), 109.7 (d), 110.1 (d), 141.5 (d), 142.9 (d), 143.2 (d), 144.3 (d).

3. 1,1'-oxybis-1-nonene, Prepared from Nonanal
MS: 266 (M$^+$, 17), 181 (12), 124 (20), 83 (65), 82 (50), 69 (100), 57 (39), 55 (47), 41 (34).
$^1$H NMR: 0.88 (t, J=6.9, 6H); 1.20-1.45 (m, 20H); 1.88-1.96 (m) and 2.06-2.16 (m) (4H); 4.47 (q, J=6.1), 4.52 (q, J=6.1), 5.04 (dt, J=12.3, J=7.2) and 5.06 (dt, J=12.3, J=7.2) (=CHR, 2H); 6.09 (d, J=6.1), 6.13 (d, J=6.1), 6.21 (d, J=12.3), 6.26 (d, J=12.3) (OCH=, 2H).
$^{13}$C NMR: 14.10 (q), 22.69 (t), 22.71 (t), 23.97 (t), 24.01 (t), 27.36 (t), 29.03 (t), 29.17 (t), 29.21 (t), 29.58 (t), 29.64 (t), 30.23 (t), 30.31 (t), 31.88 (t), 31.92 (t), 108.5 (d), 108.9 (d), 109.7 (d), 110.1 (d), 141.5 (d), 142.9 (d), 143.2 (d), 144.3 (d).

4. 1,1'-oxybis-1-undecene, Prepared from Undecanal
MS: 322 (M$^+$, 16), 209 (13), 152 (22), 97 (100), 83 (88), 69 (52), 57 (43), 55 (56), 41 (35).
$^1$H NMR: 0.88 (t, J=6.9, 6H); 1.20-1.45 (m, 28H); 1.87-1.96 (m) and 2.06-2.17 (m) (4H); 4.47 (q, J=6.1), 4.52 (q, J=6.1), 5.04 (dt, J=12.3, J=7.7) and 5.06 (dt, J=12.3, J=7.7) (=CHR, 2H); 6.09 (d, J=6.1), 6.12 (d, J=6.1), 6.21 (d, J=12.3), 6.26 (d, J=12.3) (OCH=, 2H).
$^{13}$C NMR: 14.1 (q), 22.73 (t), 24.03 (t), 27.38 (t), 29.29 (t), 29.38 (t), 29.42 (t), 29.53 (t), 29.55 (t), 29.60 (t), 29.66 (t), 30.34 (t), 31.96 (t), 31.99 (t), 108.5 (d), 108.9 (d), 109.7 (d), 110.1 (d), 141.5 (d), 142.9 (d), 143.2 (d), 144.3 (d).

5. 1,1'-oxybis-1-dodecene, Prepared from Dodecanal
MS: 350 (M$^+$, 6), 166 (30), 111 (59), 97 (100), 83 (86), 82 (64), 69 (71), 57 (47), 55 (62), 43 (50), 41 (42).
$^1$H NMR: 0.88 (t, J=6.7, 6H); 1.20-1.40 (m, 32H); 1.88-1.96 (m) and 2.05-2.16 (m) (4H); 4.47 (q, J=6.1), 4.52 (q, J=6.1), 5.04 (dt, J=12.3, J=7.7) and 5.06 (dt, J=12.3, J=7.7) (=CHR, 2H); 6.09 (d, J=6.1), 6.13 (d, J=6.1), 6.21 (d, J=12.3), 6.26 (d, J=12.3) (OCH=, 2H).
$^{13}$C NMR: 14.1 (q), 22.71 (t), 23.95 (t), 23.99 (t), 27.33 (t), 27.35 (t), 29.06 (t), 29.25 (t), 29.36 (t), 29.38 (t), 29.40 (t), 29.49 (t), 29.52 (t), 29.56 (t), 29.62 (t), 29.65 (t), 29.70 (t), 30.21 (t), 30.29 (t), 31.93 (t), 31.95 (t), 108.47 (d), 108.80 (d), 109.69 (d), 110.08 (d), 141.46 (d), 142.87 (d), 143.13 (d), 144.23 (d).

6. 1,1'-oxybis(2-methyl-1-decene), Prepared from 2-methyldecanal
MS: 322 (M$^+$, 64), 223 (38), 170 (13), 167 (11), 97 (48), 83 (54), 71 (93), 69 (52), 55 (100).
$^1$H NMR: 0.88 (t, J=6.8, 6H); 1.20-1.43 9m, 24H); 1.53 (s), 1.63 (s), 1.64 (s) (6H); 1.87 (bt, J=7.2), 2.10 (t, J=7.2), 2.12 (t, J=7.2) (4H); 5.96 (s), 5.98 (s), 6.01 (s) (OCH=, 2H).
$^{13}$C NMR: 13.0 (q), 14.1 (q), 17.1 (q), 22.72 (t), 27.27 (t), 27.36 (t), 27.96 (t), 28.98 (t), 29.09 (t), 29.27 (t), 29.36 (t), 29.41 (t), 29.44 (t), 29.53 (t), 29.55 (t), 29.60 (t), 31.97 (t), 32.01 (t), 33.76 (t), 33.79 (t), 115.53 (s), 115.75 (s), 115.81 (s), 138.52 (d), 138.57 (d), 138.73 (d), 138.78 (d).

7. 1,1'-oxybis(2-methyl-1-undecene), Prepared from 2-methylundecanal

MS: 350 (M⁺, 52), 237 (28), 184 (9), 181 (8), 97 (42), 83 (50), 71 (95), 69 (63), 55 (100), 43 (65).

¹H NMR: 0.88 (t, J=6.9, 6H); 1.19-1.45 (m, 28H); 1.53 (s), 1.63 (s), 1.64 (s) (6H); 1.87 (bt, J=7.2), 2.10 (t, J=7.2), 2.12 (t, J=7.2) (4H); 5.96 (s), 5.98 (s), 6.01 (s) (OCH=, 2H).

¹³C NMR: 13.0 (q), 14.1 (q), 17.1 (q), 22.73 (t), 27.26 (t), 27.35 (t), 27.96 (t), 28.97 (t), 29.09 (t), 29.26 (t), 29.40 (t), 29.48 (t), 29.59 (t), 29.66 (t), 29.69 (t), 29.74 (t), 31.96 (t), 33.79 (t), 115.51 (s), 115.73 (s), 115.81 (s), 138.52 (d), 138.56 (d), 138.72 (d), 138.77 (d).

8. 1,1'-[oxybis(1-propene-1,3-diyl)]dibenzene, Prepared from 3-phenylpropanal

MS: 250 (M⁺, 4), 206 (4), 159 (18), 145 (9), 131 (10), 117 (100), 115 (50), 91 (42).

¹H NMR: 3.25 (d, J=7.4), 3.27 (d, J=7.7), 3.45 (d, J=7.4), 3.50 (d, J=7.4) (4H); 4.72-4.78 (m), 5.23-5.29 (m) (=CHBn, 2H); 6.24 (d, J=6.1), 6.28 (d, J=5.8), 6.30 (d, J=12.2), 6.38 (d, J=12.2) (OCH=, 2H); 7.13-7.30 (m, 10H).

¹³C NMR: 30.2 (t), 30.4 (t), 33.5 (t), 33.6 (t), 107.55 (d), 107.65 (d), 108.66 (d), 108.89 (d), 125.84 (d), 125.85 (d), 126.11 (d), 140.59 (s), 140.67 (s), 140.99 (s), 141.05 (s), 141.05 (d), 141.89 (d), 143.28 (d), 144.17 (d), 145.21 (d).

9. 1,1'-[oxybis(3-methyl-1-propene-1,3-diyl)]dibenzene, Prepared from 3-phenylbutanal MS: 278 (M⁺, 3), 263 (38), 173 (8), 160 (14), 145 (13), 131 (100), 117 (57), 115 (49), 105 (69), 91 (68).

¹H NMR: 1.33-1.39 (overlapping doublets, 6H); 3.42 (q, J=7.2) and 3.95-4.06 (m) (2H); 4.66-4.74 (overlapping dd) and 5.30 (dd, J=12.3, J=7.7) (=CHR, 2H); 6.11 (d, J=6.1), 6.14 (d, J=6.1), 6.26 (d, J=12.3) and 6.31 (d, J=12.3) (OCH=, 2H); 7.14-7.32 (m, 10H).

¹³C NMR: 21.86 (q), 21.91 (q), 21.92 (q), 21.99 (q), 22.23 (q), 22.25 (q), 34.43 (d), 34.76 (d), 34.81 (d), 38.11 (d), 38.13 (d), 114.09 (d), 114.11 (d), 114.22 (d), 114.27 (d), 115.04 (d), 115.45 (d), 115.47 (d), 125.87 (d), 125.90 (d), 126.15 (d), 126.83 (d), 126.86 (d), 126.99 (d), 128.34 (d), 128.36 (d), 128.38 (d), 128.44 (d), 140.45 (d), 140.47 (d), 141.80 (d), 141.82 (d), 143.17 (d), 144.15 (d), 146.07 (s), 146.11 (s), 146.46 (s), 146.66 (s).

10. 1,1'-[oxybis(2-methyl-1-butene-1,4-diyl)]dibenzene, Prepared from 2-methyl-4-phenylbutanal

MS: 306 (M⁺, 11), 215 (31), 197 (4), 159 (10), 145 (39), 117 (19), 91 (100).

¹H NMR: 1.54 (s), 1.70 (s), 1.71 (s) (6H); 2.17 (bt, J=8.0), 2.39-2.44 (m) (4H), 2.65-2.73 (m) (4H), 5.93 (s), 5.94 (s), 5.95 (s) (OCH=, 2H); 7.13-7.27 (m, 10H).

¹³C NMR: 13.2 (q), 17.3 (q), 31.20 (t), 31.35 (t), 33.76 (t), 33.87 (t), 34.80 (t), 35.94 (t), 114.74 (s), 114.86 (s), 114.92 (s), 115.10 (s), 125.65 (d), 125.76 (d), 128.27 (d), 128.36 (d), 138.91 (d), 138.93 (d), 139.23 (d), 139.28 (d), 142.10 (s), 142.12 (s), 142.33 (s).

11. 1,1'-[oxybis(3-methyl-1-pentene-1,5-diyl)]dibenzene, Prepared from 3-methyl-5-phenylpentanal MS: 334 (M⁺, 1), 229 (3), 175 (4), 159 (53), 143 (12), 159 (53), 143 (12), 117 (17), 91 (100), 81 (17), 55 (11).

¹H NMR: 1.00-1.05 (overlapping doublets, 6H); 1.48-1.70 (m, 4H); 2.01-2.16 (m) and 2.50-2.79 (m) (6H); 4.31-4.42 (m) and 4.93-5.02 (m) (=CHR, 2H); 6.11-6.15 (m), 6.22 (d, J=12.3) and 6.27 (d, J=12.3) (OCH=, 2H); 7.10-7.28 (m, 10H).

¹³C NMR: 21.18 (q), 21.28 (q), 21.33 (q), 21.69 (q), 21.72 (q), 21.75 (q), 28.96 (d), 29.04 (d), 29.20 (d), 32.18 (d), 33.63 (t), 33.90 (t), 33.98 (t), 39.26 (t), 39.33 (t), 39.45 (t), 114.1 (d), 114.5 (d), 114.6 (d), 115.2 (d), 115.9 (d), 125.49 (d), 125.62 (d), 128.17 (d), 128.27 (d), 128.36 (d), 128.41 (d), 128.43 (d), 140.97 (d), 142.32 (d), 142.57 (s), 142.75 (t), 142.92 (s), 142.95 (s), 143.8 (d).

12. 1,1'-oxybis(1,6-nonadiene), Prepared from 6(E)-nonenal

MS: 262 (M⁺, <1), 123 (51), 81 (100), 67 (57), 55 (32), 41 (36).

¹H NMR: 0.95 (t, J=7.4, 6H); 1.37-1.47 (m, 4H); 1.90-2.18 (m, 12H); 4.48 (q, J=6.1) and 4.53 (q, J=6.1), 5.04 (dt, J=12.3, J=7.2) and 5.06 (dt, J=12.3, J=7.2) (=CHR, 2H); 5.27-5.40 (m, —CH=CH-Me, 4H); 6.11 (d, J=6.1), 6.14 (d, J=6.1), 6.22 (d, J=12.3), 6.27 (d, J=12.3) (OCH=, 2H).

¹³C NMR: 14.38 (q), 14.40 (q), 20.53 (t), 20.57 (t), 23.66 (t), 23.71 (t), 26.44 (t), 26.75 (t), 26.90 (t), 29.68 (t), 29.74 (t), 30.24 (t), 30.30 (t), 108.14 (d), 108.45 (d), 109.36 (d), 109.73 (d), 128.72 (d), 128.74 (d), 128.95 (d), 128.97 (d), 131.79 (d), 131.81 (d), 131.97 (d), 131.98 (d), 141.66 (d), 143.06 (d), 143.36 (d), 144.46 (d).

13. 1,1'-oxybis(3,5,5-trimethyl-1-hexene), Prepared from 3,5,5-trimethylhexanal

MS: 266 (M⁺, 23), 195 (100), 141 (25), 85 (33), 57 (99).

¹H NMR: δ 0.85-0.93 (overlapping singlets, 18H); 0.94-1.03 (overlapping doublets, 6H); 1.20-1.30 (m, 4H); 2.16-2.27 (m) and 2.73-2.92 (m) (2H); 4.31-4.48 (m) and 4.89-5.02 (m) (=CHR, 2H); 5.95 (d, J=6.1 Hz), 5.98 (d, J=12.3 Hz), 6.17 (d, J=13.2 Hz) 6.22 (d, J=12.3 Hz), 6.23 (d, J=12.3 Hz) (OCH=, 2H).

¹³C NMR: δ 23.93 (q), 24.00 (q), 24.04 (q), 24.75 (q), 24.82 (q), 24.90 (q), 25.82 (d), 25.85 (d), 25.99 (d), 29.38 (d), 29.45 (d), 30.02 (q), 30.04 (q), 30.06 (q), 30.16 (q), 31.10 (s), 31.12 (s), 31.15 (s), 51.48 (t), 51.50 (t), 51.55 (t), 51.79 (t), 51.82 (t), 51.84 (t), 116.57 (d), 117.29 (d), 117.32 (d), 117.91 (t), 117.97 (t), 119.03 (d), 139.09 (d), 139.13 (d), 140.60 (d), 140.67 (d), 141.47 (d), 141.51 (d), 142.57 (d), 142.64 (d)

14. 1,1'-oxybis(1,9-undecene), Prepared from 9-undecenal

MS: 318 (M⁺, <1), 151 (20), 150 (16), 135 (6), 109 (31), 95 (100), 83 (20), 81 (44), 69 (28), 68 (16), 67 (29), 55 (20), 41 (20).

¹H NMR: δ 1.21-1.42 (m, 16H); 1.57-1.65 (overlapping doublets, 6H); 1.86-2.18 (m, 8H); 4.46 (q, J=6.6 Hz) and 4.52 (q, J=6.5 Hz), 5.03 (dt, J=12.3, 7.4 Hz) and 5.05 (dt, J=12.3, 7.2 Hz) (=CHR, 2H); 5.32-5.48 (m, 4H); 6.09 (d, J=6.2 Hz), 6.12 (d, J=6.2 Hz), 6.20 (d, J=12.2 Hz), 6.26 (d, J=12.3 Hz) (OCH=, 2H).

¹³C NMR: δ 12.74 (q), 17.92 (q), 23.93 (t), 23.98 (t), 26.82 (t), 26.85 (t), 27.33 (t), 28.90 (t), 28.92 (t), 28.98 (t), 29.00 (t), 29.03 (t), 29.09 (t), 29.11 (t), 29.33 (t), 29.52 (t), 29.56 (t), 29.61 (t), 30.16 (t), 30.24 (t), 32.59 (t), 32.62 (t), 108.39 (d), 108.75 (d), 109.62 (d), 109.99 (d), 110.01 (d), 123.59 (d), 123.66 (d), 125.52 (d), 124.59 (d), 130.79 (d), 130.87 (d), 131.59 (d), 131.67 (d), 141.48 (d), 141.49 (d), 142.89 (d), 143.17 (d), 144.26 (d).

15. 1,1'-[oxybis(1-propene-1,3-diyl)]bis(4-tert-butylbenzene), Prepared from 3-(4-tert-butylphenyl)propanal MS: 362 (M⁺, 1), 305 (3), 215 (4), 201 (3), 173 (13), 166 (17), 159 (23), 147 (12), 117 (34), 57 (100).

¹H NMR: δ 1.30 (s), 1.303 (s), 1.31 (s) (18H); 3.24 (d), 3.26 (d, J=6.8 Hz), 3.43 (d, J=7.9 Hz), 3.28 (d, J=7.6 Hz) (4H); 4.70-4.80 (m), 5.23-5.31 (m) (2H); 6.26 (d, J=6.1 Hz), 6.30 (d, 6.0 Hz), 6.33 (d, J=12.3 Hz), 6.41 (d, J=12.3 Hz) (2H); 7.10-7.25 (m), 7.25-7.35 (m) (8H).

¹³C NMR: δ 29.7 (t), 29.8 (t), 31.4 (q), 33.0 (t), 33.03 (t), 34.3 (s), 34.4 (s), 107.6 (d), 107.8 (d), 108.8 (d), 109.1 (d), 125.26 (d), 125.28 (d), 125.3 (d), 127.95 (d), 127.97 (d), 137.6 (s), 137.7 (s), 137.9 (s), 138.0 (s), 141.8 (d), 143.2 (d), 144.1 (d), 145.1 (d), 148.7 (s), 149.0 (s).

16. 1,1'-oxybis(1,10-undecene), Prepared from 10-undecenal

MS: 318 (M+, <1), 135 (11), 121 (14), 109 (46), 95 (100), 83 (51), 81 (64), 69 (53), 67 (71), 57 (26), 55 (83), 41 (56).

$^1$H NMR: δ 1.23-1.43 (m, 20H); 1.87-2.17 (overlapping multiplets, 8H); 4.46 (q, J=6.7 Hz), 4.52 (q, J=6.8 Hz), 5.03 (d, J=10.2 Hz), 5.05 (d, J=17.1 Hz), 5.03 (dt, J=12.3, 7.4 Hz), 5.05 (dt, J=12.3, 7.4 Hz), 5.81 (ddt, J=17.1, 10.2, 6.8 Hz), 6.09 (d, J=6.2 Hz), 6.12 (d, J=6.2 Hz), 6.21 (d, J=12.3 Hz), 6.26 (d, J=12.3 Hz) (alkene protons, 10H).

$^{13}$C NMR: δ 23.92 (t), 23.97 (t), 27.33 (t), 28.94 (t), 28.95 (t), 28.97 (t), 29.10 (t), 29.12 (t), 29.16 (t), 29.31 (t), 29.32 (t), 29.52 (t), 29.58 (t), 30.19 (t), 30.26 (t), 33.81 (t), 33.82 (t), 33.84 (t), 108.42 (d), 108.77 (d), 109.62 (d), 110.02 (d), 114.10 (t), 114.14 (t), 139.16 (d), 139.21 (d), 141.49 (d), 142.89 (d), 143.18 (d), 144.27 (d).

EXAMPLES

The invention will now be described in further detail by way of the following examples, wherein the abbreviations have the usual meaning in the art and the temperatures are indicated in degrees centigrade (° C.).

These examples are not intended to be limitative and similar effect can be obtained with all of the compounds cited in the present application.

Example 1

Preparation of a Perfuming Composition

A perfuming composition (Composition A) was prepared by admixing the following ingredients.

TABLE 1

| Perfuming composition A | |
|---|---|
| Ingredients | Parts |
| Ethyl 2-methyl-pentanoate [1] | 40 |
| Undecalactone | 72 |
| Raspberry ketone Methylether | 28 |
| Cassis Base 345 B [2] | 60 |
| 3-Hydroxy-2-ethyl-4-pyrone | 4 |
| Ethylvanilline | 4 |
| Exaltolide ® [3] | 420 |
| Polysantol ® [4] | 20 |
| Verdox ® [5] | 340 |
| TOTAL | 1000 |

[1] Origin: Firmenich SA, Geneva, Switzerland
[2] Origin: Firmenich SA, Geneva, Switzerland
[3] Pentadecanolide, origin: Firmenich SA, Geneva, Switzerland
[4] 3,3-Dimethyl-5-(2',2',3'-trimethyl-3'-cyclopenten-1'-yl)-4-penten-2-ol, origin: Firmenich SA, Geneva, Switzerland
[5] 2-tert-butyl-1-cyclohexyl acetate, origin: International Flavors & Fragrances, USA.

A perfuming composition according to the invention was prepared by adding 500 parts of 1,1'-oxybis-1-decene to composition A described above.

Example 2

Preparation of a Perfuming Composition

A perfuming composition (Composition B) was prepared by admixing the following ingredients.

TABLE 2

| Perfuming composition B | |
|---|---|
| Ingredients | Parts |
| Undecalactone | 38 |
| Raspberry ketone Methylether | 13 |
| Cassis Base 345 B [1] | 158 |
| Orange terpenes [2] | 70 |
| Habanolide ® [3] | 325 |
| Linalol | 170 |
| Hedione ® [4] | 205 |
| Polysantol ® [5] | 13 |
| Undecavertol ® [6] | 8 |
| TOTAL | 1000 |

[1] Origin: Firmenich SA, Geneva, Switzerland
[2] Origin: Firmenich SA, Geneva, Switzerland
[3] Pentadecenolide, origin: Firmenich SA, Geneva, Switzerland
[4] Methyl dihydrojasmonate, origin: Firmenich SA, Geneva, Switzerland
[5] 3,3-Dimethyl-5-(2',2',3'-trimethyl-3'-cyclopenten-1'-yl)-4-penten-2-ol, origin: Firmenich SA, Geneva, Switzerland
[6] 4-Methyl-3-decen-5-ol, origin: Givaudan-Roure SA, Vernier, Switzerland.

A perfuming composition according to the invention was prepared by adding 166 parts of 1,1'-{oxybis[1-butene-1,3-diyl]}dibenzene to composition B described above.

Example 3

Preparation of an Alcoholic Deodorant and Olfactive Evaluation Thereof

The following deodorant composition was prepared in a generally known manner with the following ingredients in the proportions indicated:

TABLE 3

| Deodorant composition | |
|---|---|
| Ingredient | Weight (%) |
| De-mineralized water | 2.00 |
| Ethanol | 95.15 |
| Irgasan ® DP 300 [1] | 0.25 |
| Isopropyl Myristate | 2.60 |

[1] 5-Chloro-2-(2,4-dichlorophenoxy)phenol, origin: Ciba Chemicals

Three samples were prepared by adding to this deodorant 0.47% of 1,1'-oxybis-1-decene (sample A, according to the invention), 0.46% of nonanal (sample B, comparative) or respectively 0.50% of decanal (sample C, comparative).

An amount of 0.15 g of each sample was spread evenly on paper blotters of 4.5 cm×12 cm. The blotters were stored for 1 hour, 24 hours and 48 hours at room temperature and under ambient laboratory light.

The blotters were then evaluated olfactively on a blind test by 10 panelists who were asked to rate the fragrance strength of each sample on a scale from 0 to 10, where 0 meant no smell and 10 meant very strong smell. The data shown in Table 4 below indicates that the divinyl ethers released the free aldehydes over 48 hours and provided a stronger olfactive intensity, when compared to the corresponding free aldehydes which evaporated quickly from the blotters.

TABLE 4

Results of the olfactive evaluation

| | Average intensity on blotter | | |
|---|---|---|---|
| | 1 hour | 24 hours | 48 hours |
| Sample A | 6.6 | 7.2 | 6.7 |
| Sample B (comparative) | 6.0 | 3.5 | 2.4 |
| Sample C (comparative) | 8.5 | 4.4 | 3.7 |

Example 4

Preparation of a Body Lotion and Olfactive Evaluation Thereof

A body lotion composition was prepared in a generally known manner with the following ingredients used in the proportions indicated:

TABLE 5

Body lotion composition

| Ingredient | Weight (%) |
|---|---|
| De-mineralized water | q.s. 100 |
| Stearyl Alcohol | 2 |
| Cetearyl Alcohol | 2.5 |
| Ceteareth ®-20 | 1.5 |
| Dimethicone | 1 |
| Isopropyl myristate | 3 |
| Glycerin ® | 2.58 |
| Polyquaternium-10 | 0.05 |
| Glydant ® Plus Liquid [1] | 0.15 |
| Citric acid | q.s. pH = 5.5-6.5 |

[1] DMDM Hydantoin and Iodoproynyl butylcarbamate, origin: Lonza.

Three samples were prepared by adding to that body lotion 0.47% of 1,1'-oxybis-1-nonene (sample D, according to the invention), 0.45% of octanal (sample E, comparative) and 0.50% of nonanal (sample F, comparative).

An amount of 0.15 g of each sample was spread evenly on paper blotters of 4.5 cm×12 cm. The blotters were stored for 1 hour, 24 hours and 48 hours at room temperature and under ambient laboratory light.

The blotters were then evaluated olfactively on a blind test by 10 panelists who were asked to rate the fragrance strength of each sample on a scale from 0 to 10, where 0 meant no smell and 10 meant very strong smell. The data shown in Table 6 below indicates that the divinyl ethers released the corresponding free aldehydes over 48 hours and provided a stronger olfactive intensity, when compared to the free aldehydes which evaporated quickly from the blotters.

TABLE 6

Results of the olfactive evaluation

| | Average intensity on blotter | | |
|---|---|---|---|
| | 1 hour | 24 hours | 48 hours |
| Sample D | 3.3 | 2.9 | 4.9 |
| Sample E (comparative) | 5.0 | 1.6 | 1.7 |
| Sample F (comparative) | 6.3 | 1.3 | 0.6 |

Example 5

Preparation of a Clear Shower Gel and Olfactive Evaluation Thereof

The following shower gel composition was prepared in a generally known manner with the following ingredients used in the proportions indicated:

TABLE 7

Shower gel composition

| Ingredient | Weight (%) |
|---|---|
| De-mineralized water | q.s. 100.00 |
| EDETA B Powder [1] | 0.05 |
| Texapon ® NSA IS [2] | 27.00 |
| TEGO Betaine F 50 [3] | 8.00 |
| Plantacare ® 818 UP [4] | 4.00 |
| Sodium benzoate | 0.20 |
| Sodium salicylate | 0.20 |
| Sodium chloride | 1.20 |
| Citric acid | q.s. pH = 4.5-4.8 |

[1] Tetrasodium EDTA, origin: BASF
[2] Sodium laureth sulfate 35%, origin: Cognis
[3] Cocamidopropyl betaine, Origin: Degussa
[4] Coco Glucoside, Origin: Cognis Five samples were prepared by adding to the shower gel composition 0.5% of 1,1'-[oxybis(1-propene-1,3-diyl)]dibenzene (sample G, according to the invention), 0.48% of phenylacetic aldehyde (sample H, comparative), 0.5% of 1,1'-oxybis-1-decene (sample I, according to the invention), 0.48% of nonanal (sample J, comparative) and 0.52% of decanal (sample K, comparative).

An amount of 0.82 g of each sample was applied on wool swatches of 6 cm×11 cm. The swatches were then lathered for 30 seconds, rinsed with warm water (37° C.) for 10 seconds and then allowed to dry under ambient laboratory light.

After 2, 4, 6 and 8 hours drying, the wool swatches were evaluated olfactively on a blind test by 10 panelists who were asked to rate the fragrance strength of each sample on a scale from 1 to 7, where 1 meant no smell and 7 meant very strong smell. The data shown in Table 8 indicates that the divinyl ethers released the corresponding free aldehydes over 8 hours and provided a stronger olfactive intensity, when compared to the free aldehydes which evaporated quickly from the dried wool swatches.

TABLE 8

Results of the olfactive evaluation

| | Average odor intensity | | | |
|---|---|---|---|---|
| | 2 hours drying | 4 hours drying | 6 hours drying | 8 hours drying |
| Sample G | 2.0 | 6.0 | 6.0 | 5.5 |
| Sample H (comparative) | 7.0 | 4.5 | 2.5 | 2.7 |
| Sample I | 2.5 | 3.0 | 3.5 | 3.5 |
| Sample J (comparative) | 2.5 | 1.0 | 1.0 | 1.0 |
| Sample K (comparative) | 4.0 | 1.0 | 1.0 | 1.0 |

Example 6

Effect of Light on the Release of Active Aldehydes from Divinyl Ethers

An amount of 0.82 g of samples G and I, as prepared in Example 5, was applied on wool swatches of 6 cm×11 cm (three swatches for each sample). The swatches were lathered for 30 seconds, rinsed with warm water (37° C.) for 10 seconds and then dried either in the dark (DARK), in direct sunlight (LUX) or under ambient laboratory light (LAB).

After 8 hours, the wool swatches were evaluated olfactively on a blind test by 10 panelists who were asked to rate the fragrance strength of each sample on a scale from 1 to 7, where 1 meant no smell and 7 meant very strong smell. The data shown in Table 9 below indicates that presence of light promoted the release of the fragrance aldehyde from the corresponding divinyl ether.

TABLE 9

Results of the olfactive evaluation

| | Average odor intensity | | |
|---|---|---|---|
| | LUX | LAB | DARK |
| Sample G | 6.5 | 5.5 | 5 |
| Sample I | 4.5 | 3 | 2.5 |

Headspace analysis of the wool swatches was carried out to determine the gaseous concentration of the released aldehydes from the divinyl ethers, as a function light exposure.

Half a piece of the treated wool swatches was placed in a closed 20 ml headspace vial. The sample was equilibrated for 10 minutes at 60° C. in order to accumulate the diffused aldehydes in the gas phase. Volatile materials from the gas phase were captured with 85 mm polyacrylate fibre from Supelco. The fibre was then desorbed in GC-MS system to analyze the adsorbed amount of volatile. The GC-MS conditions were the following: GC Agilent 6890N, MS Agilent 5973N+PAL, Col. Capillary HP-5MS, 30 m×250 Mu×0.25 Mu, Pressure 80.5 kPa, Helium glow 1.2 ml/min, Detector MSD, T° 80° C., 7° C./min until 250° C. for 3 min, 1 Mu, Split 20.

Figure 2:
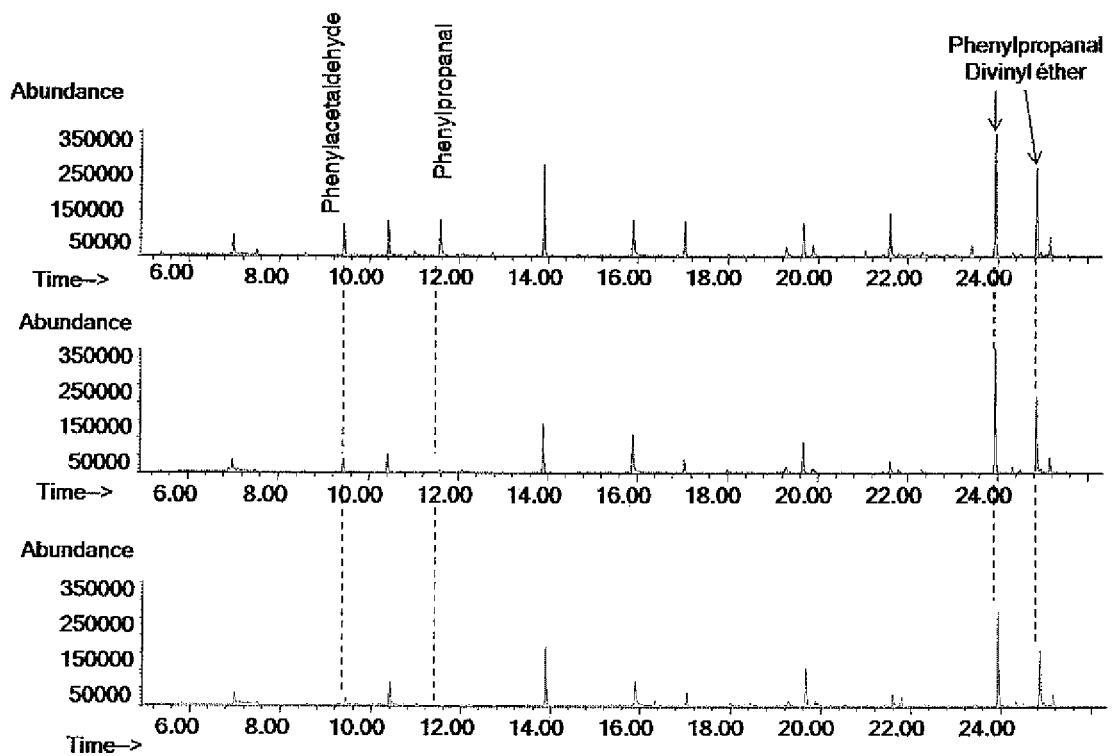

The GC-MS data shown in FIG. 1 indicated that at elevated light exposure (LUX) 1,1'-oxybis-1-decene decomposed more completely into the aldehyde decanal and nonanal. The same could be observed with 1,1'-[oxybis(1-propene-1,3-diyl)]dibenzene as shown in FIG. 2. This result confirmed the qualitative evaluation which indicated enhanced release of aldehydes in the presence of light.

Example 7

Preparation of a Pearlizing Shampoo and Olfactive Evaluation Thereof

The following pearlizing shampoo composition was prepared in a generally known manner with the following ingredients in the proportions indicated:

TABLE 10

Pearlizing shampoo composition

| Ingredient | Weight (%) |
|---|---|
| Jaguar ® C-145 [1] | 0.40 |
| Dehyton ® AB-30 [2] | 7.00 |
| Texapon ® NSO IS [3] | 45.00 |
| Dow Corning ® 2-1691 Emulsion [4] | 3.00 |
| Cutina ® AGS [5] | 0.90 |
| Rewomid ® IPP 240 [6] | 1.20 |
| Cetyl alcohol | 1.20 |
| Citric acid | q.s. pH = 6.5-7.1 |
| De-mineralized water | q.s. 100.00 |

[1] Guar Hydroxypropyltrimonium chloride, origin: Rhodia
[2] Cocobetaine, origin: Cognis
[3] Sodium laureth sulfate, origin: Cognis
[4] Dimethicone, Laureth-23, Laureth-4 and salicylic acid, origin: Dow Corning
[5] Glycol distearate, origin: Cognis
[6] Cocamide MIPA, origin: Degussa Four samples were prepared as described in Table 11 below:

TABLE 11

Preparation of the samples

| | Amount in the samples (%) | | | |
|---|---|---|---|---|
| Components | Sample L | Sample M | Sample N | Sample O |
| Pearlizing shampoo composition | 99.40 | 99.30 | 99.40 | 99.10 |
| Perfuming composition B (Table 2) | 0.60 | 0.60 | — | — |
| Perfuming composition A (Table 1) | — | — | 0.60 | 0.60 |
| 1,1'-[oxybis(1-butene-1,3-diyl)]dibenzene | — | 0.10 | — | — |
| 1,1'-oxybis-1-decene | — | — | — | 0.30 |

European brown hair swatches (10 g) were wetted for 30 seconds with warm water (37° C.), washed with 2.5 g of samples L, M, N and O for 30 seconds, with gentle rubbing between fingers to create foam. The swatches were then rinsed for 30 seconds by hand with water, washed a second time with 2.5 g of the same sample as before and rinsed for 30 seconds with water until the foam has completely disappeared from the hair and from the rinsing water. The excess of water was squeezed out of the swatches with fingertips. The treated hair swatches were allowed to dry at room temperature, under ambient laboratory light. After 6 and 24 hours, the hair swatches were evaluated olfactively on a blind test by 12 panelists who were asked to rate the fragrance strength of each sample on a scale from 1 to 7, where 1 meant no smell and 7 meant very strong smell. The data shown in Table 12 and in FIGS. 3 and 4 indicates that the aldehydes were released from the divinyl ether, when the latter was combined with a fragrance, over 6 and 24 hours.

Figure 3:
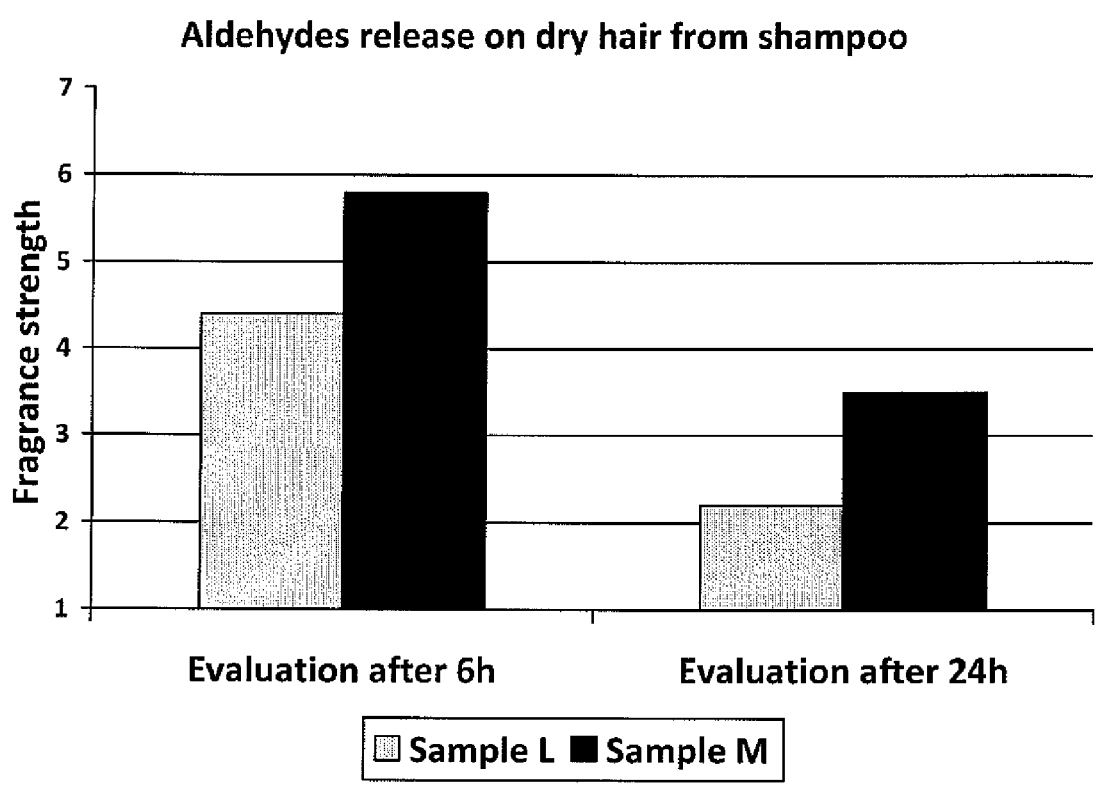

The intensity of the fragrance was lower on application of Sample L than of Sample M, after 6 and 24 hours, indicating a perceivable aldehyde release from 1,1'-[oxybis(1-butene-1,3-diyl)]dibenzene at both steps of the test (see Table 12 and FIG. 3). This was confirmed by expert panelists who could notice the green note of 3-phenylbutanal in Sample M. Intensities are decreasing from 6 to 24 hours. The olfactive intensity of composition M containing 1,1'-[oxybis(1-butene-1,3-diyl)]dibenzene remains higher than the olfactive intensity of composition L, indicating the long-lasting property of 1,1'-[oxybis(1-butene-1,3-diyl)]dibenzene.

Figure 4:
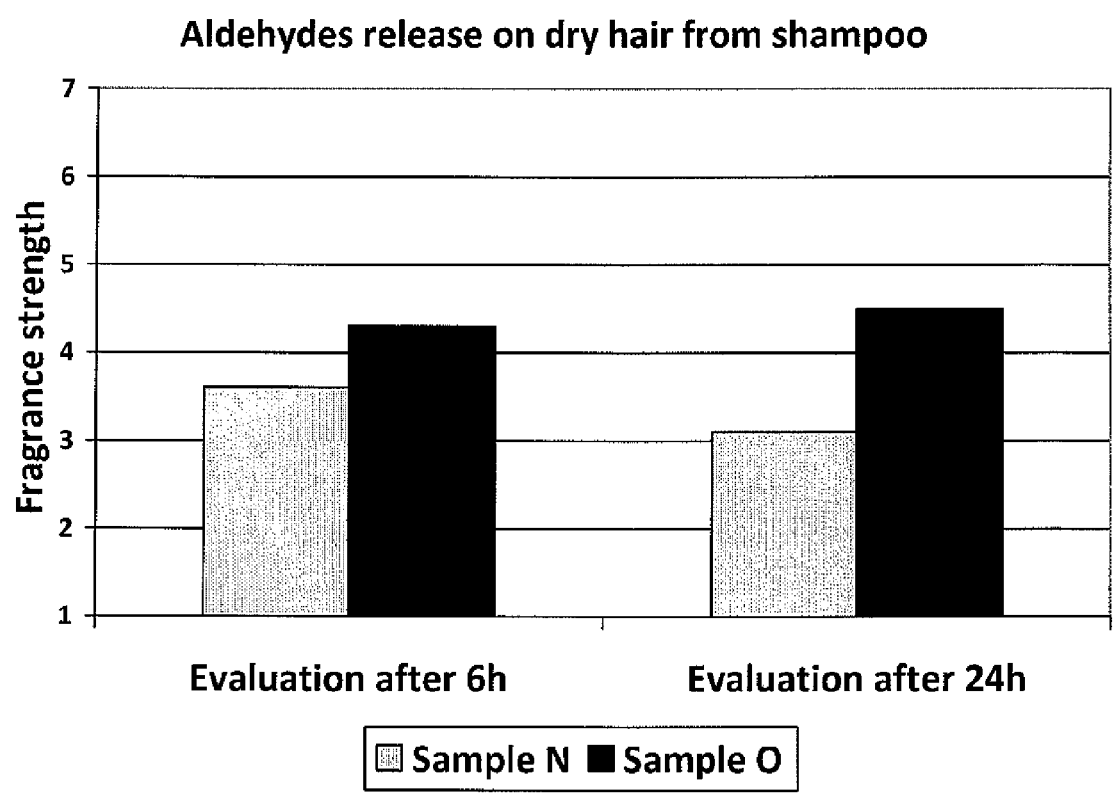

Table 12 and FIG. 4 show that while the intensity of the free fragrance (Sample N) decreased from 6 to 24 hours, the olfactive intensity of Sample 0 containing 1,1'-oxybis-1-decene increased from 6 to 24 hours which indicates the slow release of the aldehydes.

TABLE 12

Results of the olfactive evaluation

|  | Evaluation on dry hair | |
| --- | --- | --- |
|  | 6 hours | 24 hours |
| Sample L (comparative) | 4.4 | 2.2 |
| Sample M (invention) | 5.8 | 3.5 |
| Sample N (comparative) | 3.6 | 2.1 |
| Sample O (invention) | 3.1 | 4.5 |

Example 8

Preparation of a Rinse-Off Conditioner and Olfactive Evaluation Thereof

The following rinse-off conditioner composition was prepared in a generally known manner with the following ingredients in the proportions indicated:

TABLE 13

Rinse-off conditioner composition

| Ingredient | Weight (%) |
| --- | --- |
| Natrosol ® 250 H [1] | 1.00 |
| Dehyquart ® C 4046 [2] | 0.20 |
| Mirasil ® ADM-E [3] | 1.20 |
| Genamin ® KDM [4] | 1.00 |
| Crodamol SS [5] | 0.50 |
| Crodacol C90 [6] | 3.00 |
| Tetradecanol | 0.20 |
| Citric acid | q.s. pH 3.0-3.5 |
| De-mineralized water | q.s. 100 |

[1] Hydroxyethylcellulose, origin: Hercules
[2] Cetearyl alcohol and dipalmitoylethyl hydroxyethylmonium methosulfate and ceteareth-20, origin: Cognis
[3] Amodimethicone and trideceth-6, origin: Rhodia
[4] Behentrimonium chloride, origin: Clariant
[5] Cetyl esters, origin: Croda
[6] Cetyl alcohol, origin: Croda Two samples were prepared from the rinse-off conditioner composition above, with the following ingredients:

TABLE 14

Preparation of the samples

|  | Amount in the samples (%) | |
| --- | --- | --- |
| Ingredient | Sample P | Sample Q |
| Rinse-off conditioner | 99.5 | 99.48 |
| Decanal | 0.50 | — |
| 1,1'-oxybis-1-undecene | — | 0.52 |

Samples P (comparative) and Q (according to the invention) were applied on European brown hair swatches according to the following protocol: 10 g of hair swatches were wetted for 30 seconds with water at 37° C. and washed with 2.5 g of an un-perfumed shampoo such as the pearlizing shampoo prepared according to Example 7, Table 10. The hair swatches were rinsed for 30 seconds and the excess of water was squeezed out with fingertips. An amount of 1 g of samples P and Q was applied respectively on hair swatches P and Q. The hair swatches were gently rubbed between fingertips and combed with a clean comb for 1 minute. The composition was allowed to sit on the hair for two minutes. The hair swatches were then rinsed twice for 30 seconds with 37° C. water and excess water was squeezed out with fingertips. The treated hair swatches were then allowed to dry at room temperature under ambient laboratory light.

Figure 5:
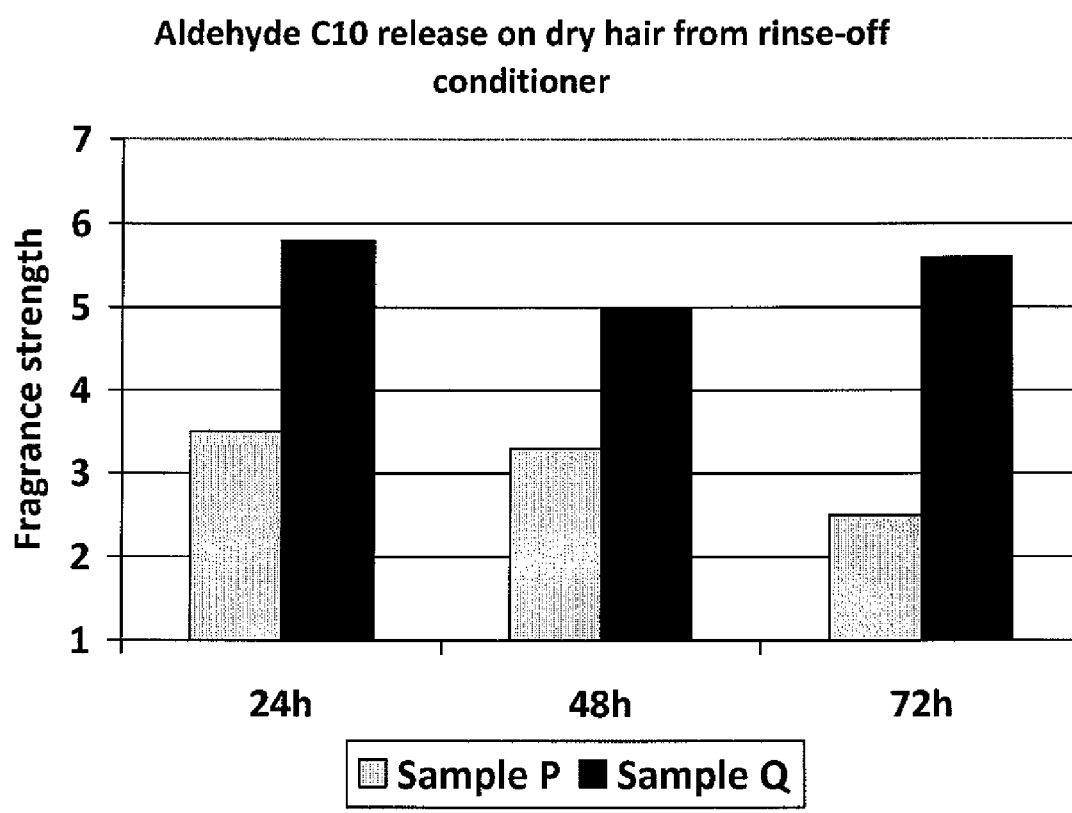

After 24 hours, 48 hours and 72 hours, the hair swatches were evaluated olfactively on a blind test by six panelists who were asked to rate the fragrance strength of each sample on a scale from 1 to 7, where 1 meant no smell and 7 meant very strong smell. The data shown in FIG. 5 and in Table 15 indicates that 1,1'-oxybis-1-undecene released the free aldehydes over 24, 48 and 72 hours and provided a stronger olfactive intensity compared to the free aldehyde which evaporated quickly from the dried hair.

TABLE 15

Results of the olfactive evaluation

|  | Average odor intensity | | |
| --- | --- | --- | --- |
|  | 24 hours | 48 hours | 72 hours |
| Sample P (comparative) | 3.5 | 3.3 | 2.5 |
| Sample Q | 5.8 | 5.0 | 5.6 |

Example 9

Preparation of a Shower Gel and Olfactive Evaluation Thereof

A shower gel composition was prepared as described in Example 5, Table 7. Six samples were prepared by adding to the shower gel composition 0.5% of 1,1'-oxybis(1,9-undecene) (sample R, according to the invention), 0.52% of 9-undecenal (sample S, comparative), 0.48% of 9-decenal (sample T, comparative), 0.5% of 1,1'oxybis(1,10-undecene) (sample U, according to the invention), 0.52% of 10-undecenal (sample V, comparative) and 0.48% of 9-decenal (sample W, comparative).

An amount of 0.50 g of each sample was applied on wool swatches of 6 cm×11 cm. The swatches were then lathered for 10 seconds, rinsed with warm water (38° C.) for 20 seconds and then allowed to dry on a hot plate (32° C.) under ambient laboratory light.

After 4 and 8 hours of drying on the hot plate, the wool swatches were evaluated olfactively in a blind test by 8 panelists who were asked to rate the fragrance strength of each sample on a scale from 1 to 10, where 1 meant no smell and 10 meant a very strong smell. The data shown in Table 16 indicates that the divinyl ethers released the corresponding free aldehydes over 8 hours and provided a stronger olfactive intensity, when compared to the free aldehydes which evaporated quickly from the dried wool swatch.

TABLE 16

Results of the olfactive evaluation

| | Average odor intensity | |
|---|---|---|
| | 4 hours drying | 8 hours drying |
| Sample R | 7.5 | 7.0 |
| Sample S (comparative) | 2.4 | 2.5 |
| Sample T (comparative) | 1.4 | 0.9 |
| Sample U | 5.7 | 5.9 |
| Sample V (comparative) | 0.4 | 0.7 |
| Sample W (comparative) | 0.7 | 0.6 |

Example 10

Decomposition of Divinyl Ethers

A series of paper blotters (6×0.7 cm) were each loaded with 40 ml of a divinyl ether using a positive displacement pipette. The following divinyl ethers were tested: 1,1'-[oxybis(1-propene-1,3-diyl)]dibenzene (divinyl ether prepared from 3-phenylpropanal), 1,1'-[oxybis(1-butene-1,3-diyl)]dibenzene (divinyl ether prepared from 3-phenylbutanal), 1,1'-oxybis(1,9-undecene) (divinyl ether prepared from 9-undecenal), 1,1'oxybis-1-decene (divinyl ether prepared from decanal) and 1,1'-oxybis(2-methyl-1-undecene) (divinyl ether prepared from 2-methylundecanal).

Each blotter was placed inside a 15 ml clear glass vial (Supelco, 27159) and sealed with a septum-equipped screw cap. The vials were purged with oxygen (20-26 ml/min) for one minute and then placed 10 inches away from a 365 nm UV-A lamp (UVP, 95-0042-07). Periodically a vial was retrieved and 1 ml of the internal standard solution (40 mg/ml of dodecane in acetone) was injected through the septum into the vial. After shaking the vial by hand, the cap was removed and another 15 ml of acetone (graduated cylinder) was added. The vial was recapped, agitated by hand for 1 minute, and then allowed to sit for another 9 minutes. The acetone solution was analyzed by GC-FID utilizing a 30 m×0.25 mm (25 μm film) HP-1 column and an Agilent 6850 gas chromatograph. The oven temperature was set to 100° C. and raised of 30° C./minute to 140° C., then by 2° C./minute to 150° C., then by 40° C./minute to 280° C. and finally hold for 3 minutes at this temperature.

Figure 6:
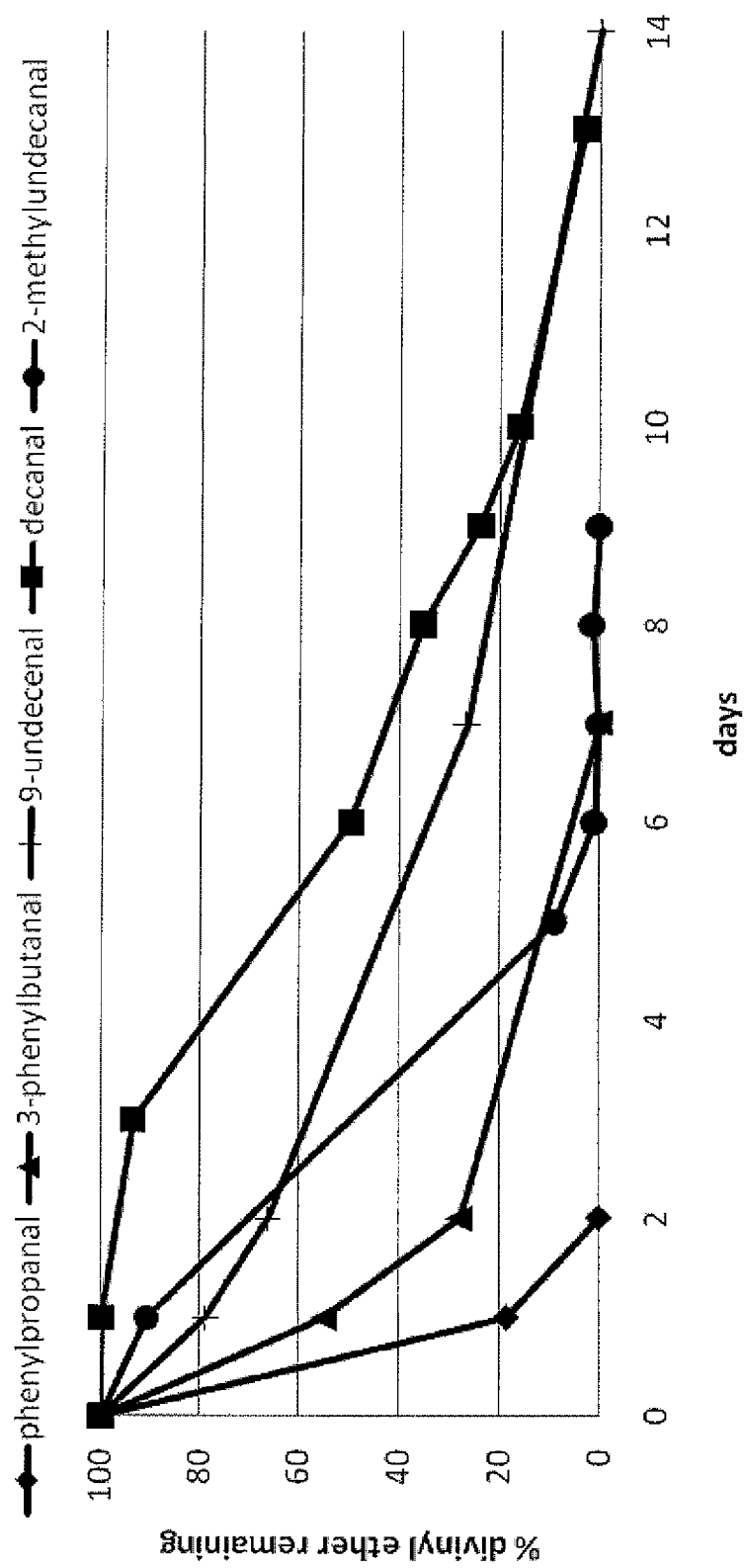
FIG. 6 is a graph that shows the release of volatiles over time.
Figure 7:
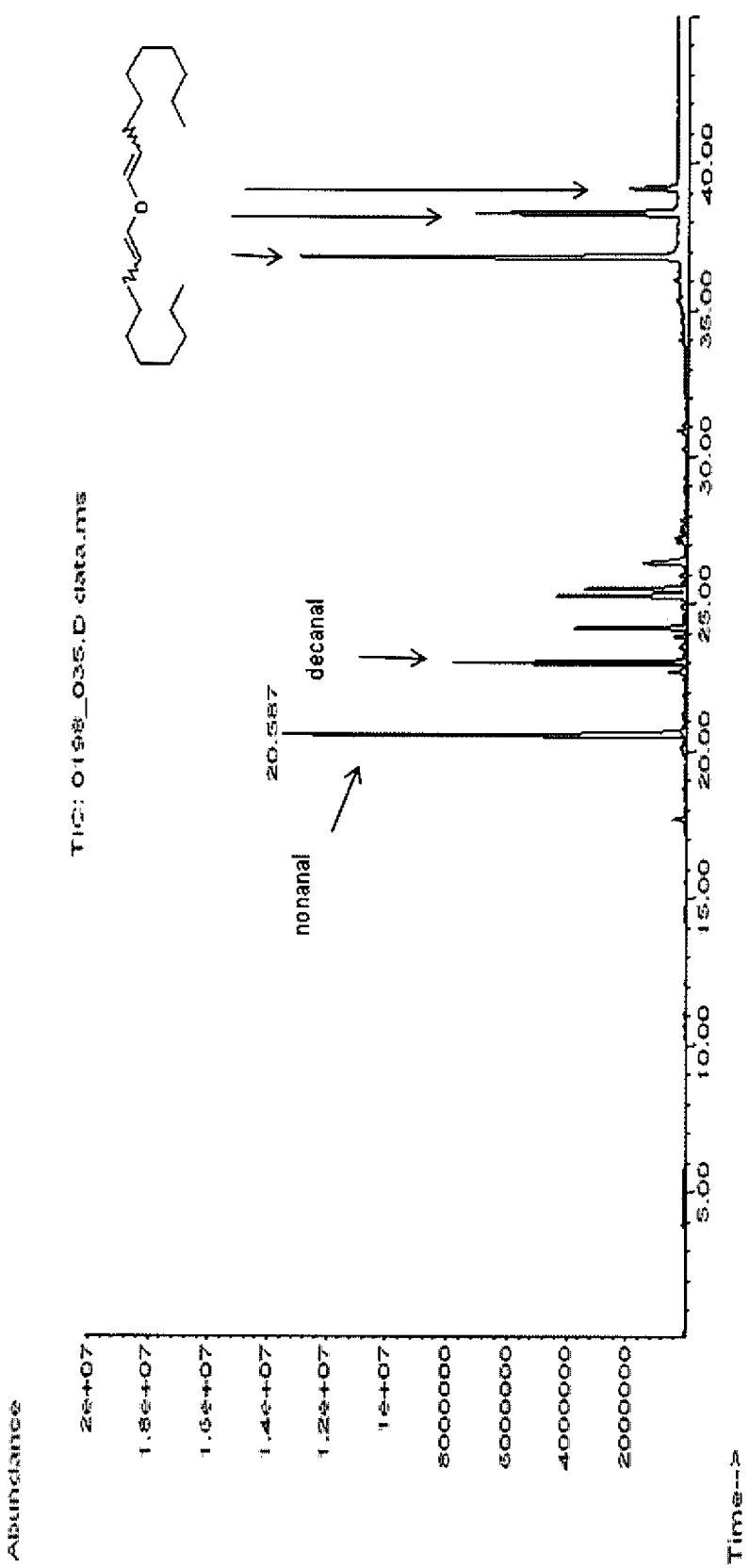
FIGS. 7 to 11 illustrate total ion chromatograms obtained from the various divinyl ethers that were tested as described herein.
Figure 8:
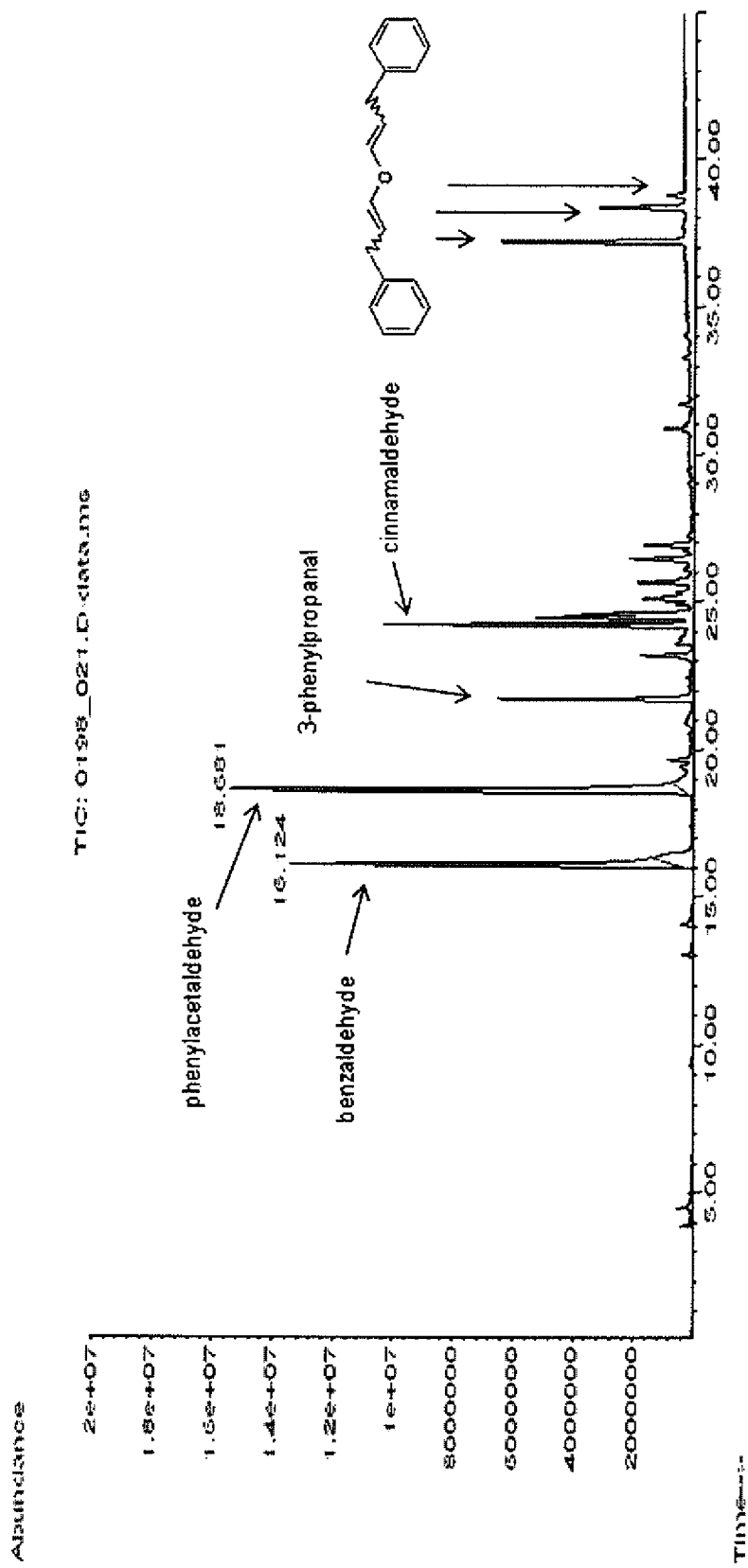
Figure 9:
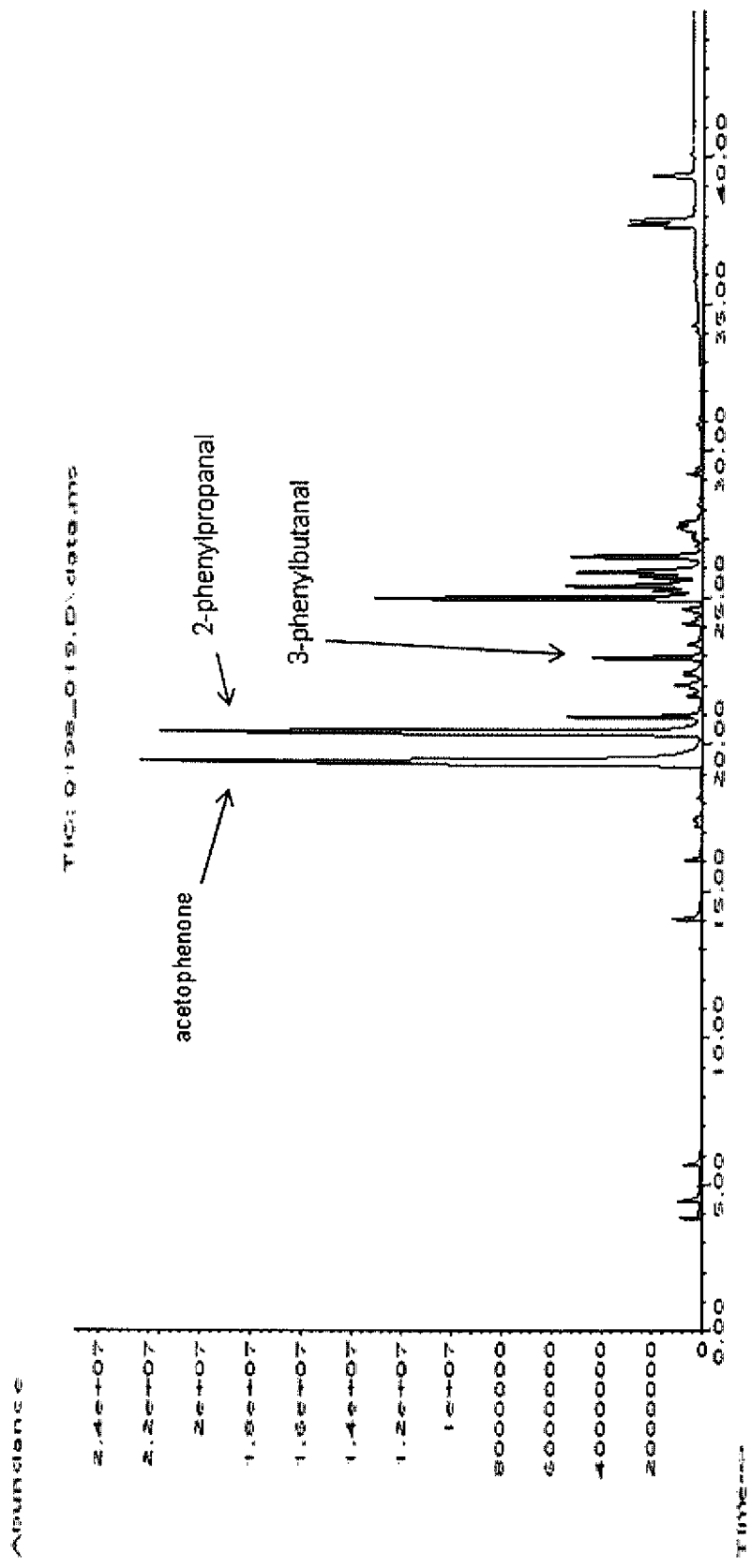
Figure 10:
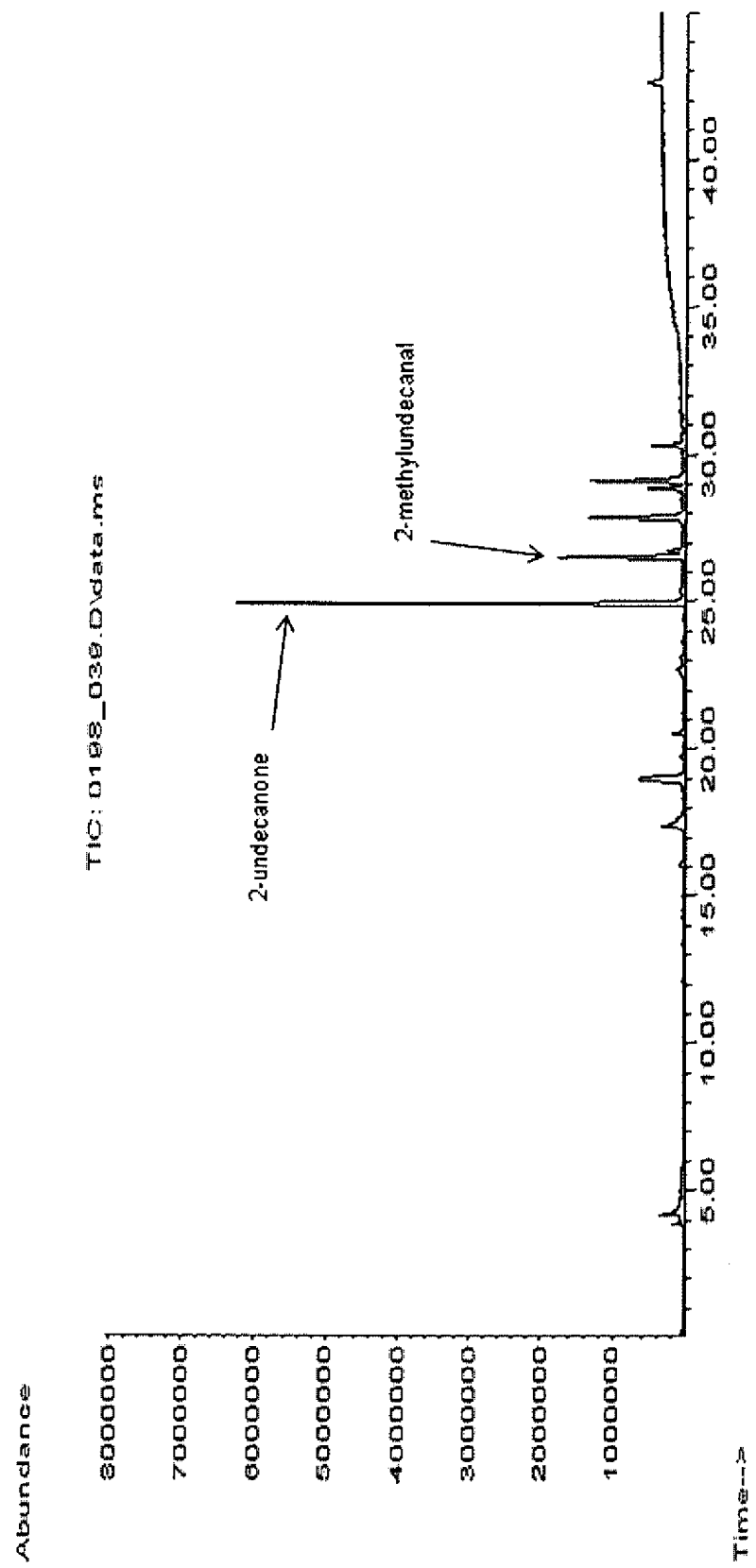
Figure 11:
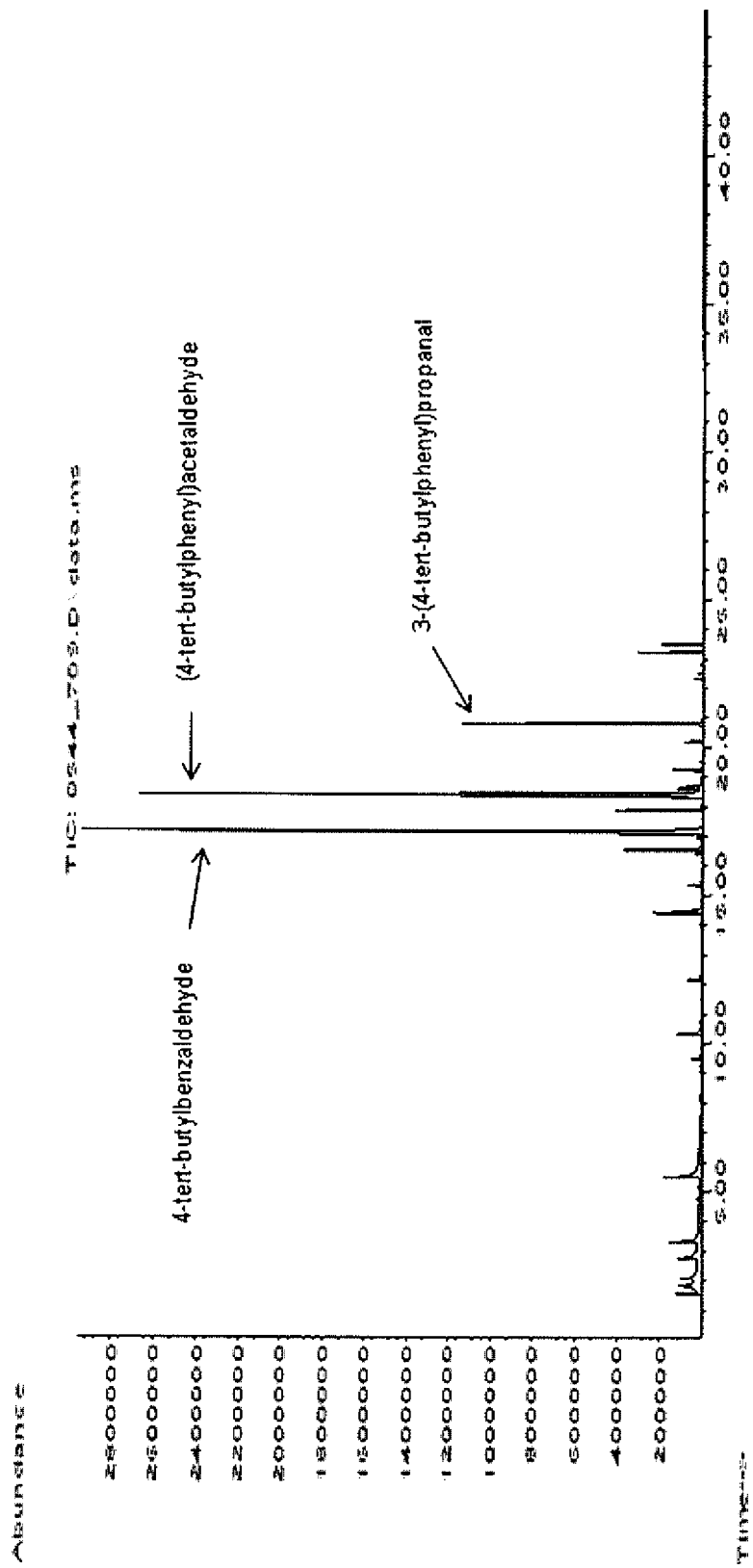

The amount of remaining divinyl ether was determined by a comparison of the GC peak areas to that of the internal standard and is reported as the percent remaining relative to the initial analysis at time zero. FIG. 6 presents the loss of each divinyl ether. This graph shows that the volatiles are released progressively over a period of 2 to 14 days.

GC-MS analyses of these extracts also revealed the formation of volatile compounds. The most abundant volatile compound formed by the decomposition of each divinyl ether is indicated in the Table 17.

TABLE 17

Most abundant volatiles released by the tested divinyl ethers

| Divinyl ether | Most abundant volatile released |
|---|---|
| 1,1'-[Oxybis(1-propene-1,3-diyl)]dibenzene | Phenylacetaldehyde |
| 1,1'-[oxybis(1-butene-1,3-diyl)]dibenzene | Acetophenone |
| 1,1'-oxybis(1,9-undecene) | 8-decenal |
| 1,1'oxybis-1-decene | Nonanal |
| 1,1'-oxybis(2-methyl-1-undecene) | 2-Decanone |

Example 11

Analysis of Volatiles Released by Divinyl Ethers

The formation of volatile products was shown by performing headspace analysis of paper blotters (6×0.7 cm) loaded with a divinyl ether and aged for 1-5 days. The tested divinyl ethers were 1,1'-oxybis-1-decene, 1,1'-[oxybis(1-propene-1,3-diyl)]dibenzene, 1,1'-[oxybis(1-butene-1,3-diyl)]dibenzene, 1,1'-oxybis(2-methyl-1-undecene) and 1,1'-[oxybis(1-propene-1,3-diyl)]bis(4-tert-butylbenzene).

Just the tips of the blotters were dipped into the divinyl ether samples. The blotters were then supported so that the tips were exposed to ambient laboratory conditions. After aging for the specified time, the blotters were sealed in a 20 ml vial with a septum-equipped cap. The headspace was equilibrated at 40° C. and the headspace sampled for 30 minutes with a 2 cm StableFlex™ fiber (Supelco) inserted into the vial through the septum. The fiber then was desorbed (250° C., 5 minutes) into a GC-MS system (Agilent 6890N coupled with a 5973 mass selective detector) equipped with a 30 m×0.25 mm (0.25 μm film) DB-1 capillary column. The oven temperature was kept at 50° C. during 3 minutes, then raised of 6° C./minute to 240° C. and finally kept at this temperature during 10 minutes. FIGS. 7 to 11 are the total ion chromatograms obtained from the tested divinyl ethers. The chromatograms show the appearance of volatile compounds as a result of exposure to the ambient atmosphere. Table 18 lists the different volatiles released by each divinyl ether.

TABLE 18

Volatiles released by each tested divinyl ether

| Divinyl Ether | Days of exposure | Released volatiles |
|---|---|---|
| 1,1'-oxybis-1-decene | 1 | Nonanal<br>Decanal |
| 1,1'-[oxybis(1-propene-1,3-diyl)]dibenzene | 1 | Benzaldehyde<br>Phenylacetaldehyde<br>3-Phenylpropanal<br>Cinnamaldehyde |
| 1,1'-[oxybis(1-butene-1,3-diyl)]dibenzene | 5 | Acetophenone<br>2-Phenylpropanal<br>3-Phenylbutanal |
| 1,1'-oxybis(2-methyl-1-undecene) | 1 | 2-Undecanone<br>2-Methylundecanal |
| 1,1'-[oxybis(1-propene-1,3-diyl)]bis(4-tert-butylbenzene) | 2 | 4-Tert-butylbenzaldehyde<br>(4-Tert-butyl-phenyl)acetaldehyde,<br>3-(4-Tert-butyl-phenyl)propanal |

What is claimed is:

1. A compound selected from the group consisting of 1,1'-oxybis-1-decene, 1,1'-oxybis-1-octene, 1,1'-oxybis-1-nonene, 1,1'-oxybis-1-undecene, 1,1'-oxybis(2-methyl-1-decene), 1,1'-oxybis(2-methyl-1-undecene), 1,1'-[oxybis(1-propene-1,3-diyl)]dibenzene, 1,1'-[oxybis(1-butene-1,3-diyl)]dibenzene, 1,1'-[oxybis(2-methyl-1-butene-1,4-diyl)]dibenzene, 1,1'-[oxybis(3-methyl-1-pentene-1,5-diyl)]dibenzene, 1,1'-oxybis(1,6-nonadiene), 1,1'-oxybis(3,5,5-trimethyl-1-hexene), 1,1'-oxybis(1,9-undec-diene), 1,1'-oxybis(1,10-undec-diene) and 1,1'-[oxybis(1-propene-1,3-diyl)]bis(4-tert-butylbenzene).

2. A compound according to claim 1, selected from the group consisting of 1,1'-[oxybis(1-propene-1,3-diyl)]dibenzene, 1,1'-[oxybis(1-butene-1,3-diyl)]dibenzene, 1,1'-[oxybis(3-methyl-1-pentene-1,5-diyl)]dibenzene and 1,1'-oxybis(1,9-undec-diene).

3. A perfuming composition comprising:
a) at least one compound of Formula (I):

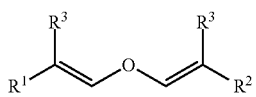

wherein $R^1$ and $R^2$ are identical or different and represent each a $C_2$ to $C_{15}$ hydrocarbon group and both $R^3$ represent, independently from each other, a hydrogen atom or a methyl group, provided that compounds of Formula (I), wherein $R^1$ is a $C_8$ mono alkenyl group and $R^2$ is selected from the group consisting of the $C_4$ to $C_{10}$ alkyl groups and the $C_9$ 8-alkenyl group, are excluded;
b) at least one ingredient selected from the group consisting of a perfumery carrier and a perfumery base; and
c) optionally at least one perfumery adjuvant.

4. A consumer article, comprising:
a) as active ingredient, at least one compound of Formula (I):

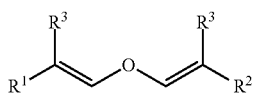

wherein $R^1$ and $R^2$ are identical or different and represent each a $C_2$ to $C_{15}$ hydrocarbon group and both $R^3$ represent, independently from each other, a hydrogen atom or a methyl group, provided that compounds of Formula (I), wherein $R^1$ is a $C_8$ mono alkenyl group and $R^2$ is selected from the group consisting of the $C_4$ to $C_{10}$ alkyl groups and the $C_9$ 8-alkenyl group, are excluded; and
b) a consumer product base.

5. A consumer article according to claim 4, in the form of a solid or liquid detergent, a fabric softener, a perfume, a cologne, an after-shave lotion, a perfumed soap, shower or bath salt, mousse, cream, oil or gel, a hygiene product, a hair care product such as a shampoo, a body-care product, a deodorant or antiperspirant, an air freshener, a cosmetic preparation, a fabric refresher, an ironing water, paper, wipe or bleach.

6. A method to confer, enhance, improve or modify odor properties of a surface, comprising contacting or treating the surface with a compound of Formula (I) under conditions sufficient to release aldehyde or ketone compounds therefrom, wherein Formula (I) is:

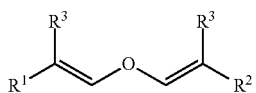

wherein $R^1$ and $R^2$ are identical or different and represent each a $C_2$ to $C_{15}$ hydrocarbon group and both $R^3$ represent, independently from each other, a hydrogen atom or a methyl group, provided that compounds of Formula (I), wherein $R^1$ is a $C_8$ mono alkenyl group and $R^2$ is selected from the group consisting of the $C_4$ to $C_{10}$ alkyl groups and the $C_9$ 8-alkenyl group, are excluded.

7. The method of claim 6, wherein the compound is applied to the surface in a perfuming composition comprising the compound, at least one ingredient selected from the group consisting of a perfumery carrier and a perfumery base; and optionally at least one perfumery adjuvant, or in an article comprising the compound and a consumer product base.

8. The method of claim 6, wherein the compound that is released is an aldehyde of Formula (II):

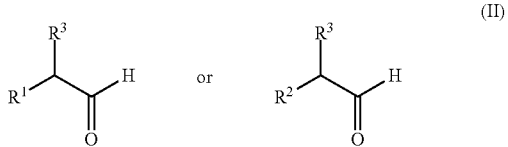

wherein $R^1$ and $R^2$ are identical or different and represent each a $C_2$ to $C_{15}$ hydrocarbon group and both $R^3$ represent, independently from each other, a hydrogen atom or a methyl group.

9. The method of claim 6, wherein the compound that is released is a ketone of Formula (III):

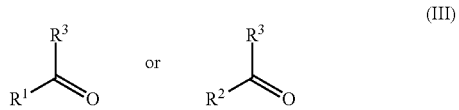

wherein $R^1$ and $R^2$ are identical or different and represent each a $C_2$ to $C_{15}$ hydrocarbon group optionally comprising an oxygen atom and both $R^3$ represent, independently from each other, a hydrogen atom or a methyl group.

10. The method of claim 6, wherein the surface treatment is carried out in the presence of light.

11. The method of claim 6, wherein $R^1$ and $R^2$ are identical and represent a $C_2$ to $C_{15}$ hydrocarbon group.

12. The method of claim 11, wherein $R^1$ and $R^2$ represent
a) a C6 to C15 linear, branched or cyclic alkyl or alkenyl group;
b) a C2 to C9 linear, branched or cyclic alkyl or alkenyl group substituted with one or more phenyl groups;
c) a benzyl group, optionally substituted with up to 8 carbon atoms; or
d) a phenyl group, optionally substituted with up to 9 carbon atoms.

13. The method of claim 12, wherein $R^1$ and $R^2$ represent
a) a C6 to C11 linear, branched or cyclic alkyl or alkenyl group;
b) a C2 to C6 linear, branched or cyclic alkyl or alkenyl group;
c) a benzyl group; or
d) a phenyl group.

14. The method of claim 13, wherein R1 and R2 represent
a) a C6 to C10 linear, branched or cyclic alkyl or alkenyl group;
b) a C2 to C4 linear, branched or cyclic alkyl or alkenyl group, substituted with one phenyl group;
c) a benzyl group; or
d) a phenyl group.

15. The method of claim 6, wherein the compound of formula (I) is selected from the group consisting of from the group consisting of 1,1'-oxybis-1-decene, 1,1'-oxybis-1-octene, 1,1'-oxybis-1-nonene, 1,1'-oxybis-1-undecene, 1,1'-oxybis(2-methyl-1-decene), 1,1'-oxybis(2-methyl-1-undecene), 1,1'-[oxybis(1-propene-1,3-diyl)]dibenzene, 1,1'-[oxybis(1-butene-1,3-diyl)]dibenzene, 1,1'-[oxybis(2-methyl-1-butene-1,4-diyl)]dibenzene, 1,1'-[oxybis(3-methyl-1-pentene-1,5-diyl)]dibenzene, 1,1'-oxybis(1,6-nonadiene), 1,1'-oxybis(3,5,5-trimethyl-1-hexene), 1,1'-oxybis(1,9-undec-diene), 1,1'-oxybis(1,10-undec-diene) and 1,1'-[oxybis(1-propene-1,3-diyl)]bis(4-tert-butylbenzene).

16. The method of claim 6, wherein the compound of formula (I) is selected from the group consisting of 1,1'-[oxybis(1-propene-1,3-diyl)]dibenzene, 1,1'-[oxybis(1-butene-1,3-diyl)]dibenzene, 1,1'-[oxybis(3-methyl-1-pentene-1,5-diyl)]dibenzene, 1,1'-oxybis(1,9-undec-diene), 1,1'-oxybis-1-decene, 1,1'-oxybis-1-nonene, or 1,1'-{oxybis[1-propene-1,3-diyl]}dibenzene.

\* \* \* \* \*